US006555366B1

(12) United States Patent
Lereclus et al.

(10) Patent No.: US 6,555,366 B1

(45) **Date of Patent: *Apr. 29, 2003**

(54) NUCLEOTIDE SEQUENCES FOR THE CONTROL OF THE EXPRESSION OF DNA SEQUENCES IN A CELL HOST

(75) Inventors: Didier Lereclus, Paris (FR); Herve Agaisse, Paris (FR)

(73) Assignees: Institut Pasteur, Paris (FR); Institut National de la Recherche Agronomique, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/503,252

(22) Filed: Feb. 14, 2000

Related U.S. Application Data

(63) Continuation of application No. 08/535,057, filed on Dec. 20, 1995, now Pat. No. 6,140,104.

(30) Foreign Application Priority Data

May 5, 1993 (FR) .......................................... 93/05387

(51) Int. Cl.[7] ......................... C12N 15/63; C12N 5/00; C07H 21/00

(52) U.S. Cl. .................. 435/320.1; 435/325; 536/23.1; 536/24.1

(58) Field of Search .............................. 435/320.1, 325; 536/23.1, 24.1

(56) References Cited

U.S. PATENT DOCUMENTS 6,344,338 B1 2/2002 Bowen et al.

OTHER PUBLICATIONS

Hofte et al. Nucleotide sequence of a gene encoding an insecticidal protein of Bacillus thuringensis var. tenebronis toxic against Coleoptera. Nuc. Acids. Res. vol. 15(17):7183, 1987.*

Donovan et al. Isolation and characterization of EF2158, a new strain of Bacillus thuingiensis toxic to coleopteran larvae, and nucleotide sequence of the toxin gene. Mol. Gen. Genet. vol. 214:365–372, 1988.*

* cited by examiner

*Primary Examiner*—Terry McKelvey
*Assistant Examiner*—William Sandals
(74) *Attorney, Agent, or Firm*—Oblon, Spivak, McClelland, Maier & Neustadt, P.C.

(57) ABSTRACT

The present invention provides nucleotide sequences from Bacillus bacteria, which control the expression of other DNA sequences in a cell host.

44 Claims, 13 Drawing Sheets

```
  1 AAGCTTTCAG TGAAGTACGT GATTATACGG AGATGAAAAT TCGTACACTG TTAACGAGAA
 61 GGAAACGCCG ACGAAAGCGT AGCATCGGAT GGCAAAGATG GAGTAACGAA TATCTCTACG
121 GTGTACTGGG GCTTTACTGA GACTAGAAAG TCCTTCCCTT GAAAAGTGCA GAGAGTTTTC
181 GATAAAAGTG TCAGCCATTT GATAAGTCTC ATTCTCATAA CCTATTGATG AAGTTTATAG
241 GGAAGCTGCT TGAGAGGGAA AACCTCACGA ACAGTTCTTA TGGGGAGAGA CTGGAAACAG
301 GTCACAATTG ATACCTCGCT AATCTTTTAA CCGACAAAGT TTTTTTAAAC CGTGGAAGTC
361 ATAATAACCT GGATATTGTG AATTTATAAA AGTTAACAAA TGGTTTATAT TAAGACAGTC
421 ATAAACCAAA GATTTTTCTT CTAAAGCTAC GATAGCAAAA ATTTCACTAG AAATTAGTTA
481 TACAAGCATT TTGTAAGAAT TATTAAAAAG ATAAATCCTG CTATTACGAG ATTAGTAGGA
541 TGATATTGTG AAAAATTTTT TATCTATTCG ATTTAAAATA TTTATGAATT TTACATAAAC
601 CTCATAAGAA AAAATACTAT CTATACTATT TTAAGAAATT TATTAGAATA AGCGGATTCA
661 AAATAGCCCT GGCCATAAAA GTACCTCAGC AGTAGAAGTT TTGACCAAAA TTAAAAAAAT
721 ACCCAATCAA GAGAATATTC TTAATTACAA TACGTTTTGC GAGGAACATA TTGATTGAAA
781 TTTAATAAAT TTAGTCCTAA AATTTAAAGA AATTTAAGTT TTTCATATTT TTATGAACTA
841 ACAAGAATAA AAATTGTGTT TATTTATTAT TCTTGTTAAA TATTTGATAA AGAGATATAT
901 TTTTGGTCGA AACGTAAGAT GAAACCTTAG ATAAAAGTGC TTTTTTTGTT GCAATTGAAG
961 AATTATTAAT GTTAAGCTTA ATTAAAGATA ATATCTTTGA ATTGTAACGC CCCTCAAAAG
```

*FIG. 3B*

```
1021  TAAGAACTAC AAAAAAAGAA TACGTTATAT AGAAATATGT TTGAACCTTC TTCAGATTAC
1081  AAATATATTC GGACGGACTC TACCTCAAAT GCTTATCTAA CTATAGAATG ACATACAAGC
1141  ACAACCTTGA AAATTTGAAA ATATAACTAC CAATGAACTT GTTCATGTGA ATTATCGCTG
1201  TATTTAATTT TCTCAATTCA ATATATAATA TGCCAATACA TTGTTACAAG TAGAAATTAA
1261  GACACCCTTG ATAGCCTTAC TATACCTAAC ATGATGTAGT ATTAAATGAA TATGTAAATA
1321  TATTTATGAT AAGAAGCGAC TTATTTATAA TCATTACATA TTTTTCTATT GGAATGATTA
1381  AGATTCCAAT AGAATAGTGT ATAAATTATT TATCTTGAAA GGAGGGATGC CTAAAAACGA
1441  AGAACATTAA AAACATATAT TTGCACCGTC TAATGGATTT ATGAAAAATC ATTTTATCAG
1501  TTTGAAAATT ATGTATTATG ATAAGAAAGG GAGGAAGAAA AATGAATCCG AACAATCGA
1560  AGTGAACAT  GATACAATA  AAAACTACT  GAAAATAAT  GAGGTGCCA  ACTAACCAT
1614  GTTCAATAT  CCTTTAGCG  GAAACTCCA  AATCCAACA  CTAGAAGAT  TTAAATTAT
1668  AAAGAGTTT  TTAAGAATG  ACTGCAG
```

*FIG. 3C*

| PLASMIDS (pHT*** lacZ) | β-GALACTOSIDASE SPECIFIC ACTIVITY (u/mg OF PROTEIN) $t_0$ | $t_6$ |
|---|---|---|
| 7830 | 3.000 | 35.000 |
| 7832 | 3.000 | 13.000 |
| 7832 ΔMunI | 10 | 30 |
| 7830 ΔMunI | 25 | 450 |
| 7815/8 | 3.000 | 42.000 |
| 7831 | 10.000 | 45.000 |

| PLASMIDS (pHT *** lacZ) | β-GALACTOSIDASE SPECIFIC ACTIVITY (u/mg OF PROTEIN) $t_3$ |
|---|---|
| 7830 | 50.000 |
| 7816 | 25.000 |
| 7805 | 5.000 |
| 7830Rm | 5.000 |

| | |
|---|---|
| | 10 * 20 * 30 * 40 * |
| 1 | GGAGGAAAAGCTGTGGAGAAAATTAAAGTATGTCTTGTGG |
| 41 | ATGATAATAAAGAATTAGTATCAATGTTAGAGAGCTATGT |
| 81 | AGCCGCCCAAGATGATATGGAAGTAATCGGTACTGCTTAT |
| 121 | AATGGTCAAGAGTGTTTAAACTTATTAACAGATAAGCAAC |
| 161 | CTGATGTACTCGTTTTAGACATTATTATGCCACACTTAGA |
| 201 | TGGTTTAGCTGTATTGGAAAAAATGCGACATATTGAAAGG |
| 241 | TTAAAACAGCCTAGCGTAATTATGTTGACAGCATTCGGGC |
| 281 | AAGAAGATGTGACGAAAAAAGCAGTTGACTTAGGTGCCTC |
| 321 | GTATTTCATATTAAAACCATTTGATATGGAGAATTTAACG |
| 361 | AGTCATATTCGTCAAGTGAGTGGTAAAGCAAACGCTATGA |
| 401 | TTAAGCGTCCACTACCATCATTCCGATCAGCAACAACAGT |
| 441 | AGATGGAAAACCGAAAAACTTAGATGCGAGTATTACGAGT |
| 481 | ATCATTCATGAAATTGGTGTACCCGCTCATATTAAAGGAT |
| 521 | ATATGTATTTACGAGAAGCAATCTCCATGGTATACAATGA |
| 561 | TATCGAATTATTAGGATCGATTACGAAAGTATTGTATCCA |
| 601 | GATATCGCAAAGAAATATAATACAACAGCCAGCCGTGTGG |
| 641 | AGCGCGCAATTCGTCACGCAATTGAAGTAGCTTGGAGCCG |
| 681 | TGGGAATATTGATTCTATTTCGTCCTTATTCGGTTATACA |
| 721 | GTATCCATGTCAAAAGCAAAACCTACGAACTCTGAGTTTA |
| 761 | TCGCAATGGTTGCGGATAAGCTGAGACTTGAACATAAAGC |
| 801 | TAGT*** |

FIG. 11B

NUCLEOTIDE SEQUENCES FOR THE CONTROL OF THE EXPRESSION OF DNA SEQUENCES IN A CELL HOST

The present application is a Continuation of U.S. Ser. No. 08/535,057, filed Dec. 20, 1995, now U.S. Pat. No. 6,140, 104, which also claims priority to FR 93/05387 filed May 5, 1993.

The object of the invention is nucleotide sequences of bacteria, in particular Gram$^+$ bacteria such as bacteria of the Bacillus type and more particularly nucleotide sequences of the cryIIIA gene for the control of the expression of DNA sequences in a cell host.

The cryIIIA gene codes for a toxin specific for the Coleoptera and is weakly expressed by *Bacillus thuringiensis* when it is cloned in a low copy number plasmid.

*Bacillus thuringiensis* is a Gram-positive bacterium which produces significant quantities of proteins in the form of crystals having a toxic activity towards insect larvae. Two groups of crystal proteins are known, based on the amino acid sequences and the toxicity specificities:

1) the class of the Cry toxins (I, II, III, etc . . . ) which have similar structures;
2) the class of the Cyt toxins, which is not related to the Cry class (Höfte, H et al. 1989, Microbiol. Rev. 53: 242–255)

These toxins of *B. thuringiensis* are of general interest for the purpose of the development of bio-pesticides and also in as much as the synthesis of crystal proteins is known to be perfectly co-ordinated with the sporulation phase of the organism, making this organism interesting for the study of genetic regulation in sporulating Gram-positive bacteria.

Various mechanisms implicated in the regulation of the synthesis of the crystal proteins of *B. thuringiensis* have been described. The high level of expression of these proteins is attributed, at least in part, to the stability of the mRNA. Some authors have attributed the stability of this mRNA to the presence downstream from the gene for the toxin of a structure playing a terminator role which might act as a positive retro-regulator by protecting the 3' end of the mRNA from degradation by nucleases, thus increasing the half-life of the transcripts (Wong, H. C. et al., 1986 Proc. Natl. Acad. Sci. USA 83: 3233–3237).

A hypothesis has also been put forward concerning the presence of polypeptides implicated in the synthesis of crystal proteins, polypeptides which are supposed to act either by directing the folding of the protein in the form at a protein having a stable conformation or to protect these proteins from proteolytic degradation.

Studies with the electron microscope and biochemical studies of sporulation in *B. thuringiensis* show that the production of the crystal protein is dependent on sporulation and is located in the mother cell compartment (Ribier, J. et al. 1973 Ann. Inst. Pasteur 124A: 311–344).

Recently, two sigma factors, sigma 35 and sigma 28, which specifically direct the transcription of the cryIA genes have been isolated and characterized. These amino acid sequences exhibit an identity of 88 and 85% with the sigma factors E and K of *Bacillus subtilis*, respectively (Adams, L. F., 1991, J. Bacteriol. 173: 3846–3854). These sigma factors are produced exclusively in sporulating cells and are capable of functioning in the mother cell compartment, confirming that the expression of the genes for the crystal protein is controlled in time and space. Thus, in the prior art it has been concluded that the expression of the gene with time is, at least in part, ensured by the successive activation of the sigma factors specific for sporulation. Hitherto, three groups of promoters have been identified. Two of these groups include promoters recognized by specific sigma factors and, according to the prior art, the sigma factors associated with the third group of promoters (including that of the cryIIIA gene) have not been identified (Lereclus, D., et al. 1989 American Society for Microbiology, Washington, D.C.).

Finally, the copy number of the plasmid bearing the gene seems to be an important factor for the expression of the cry gene in *B. thuringiensis*. In the *B. thuringiensis* wild type strain, the cry genes are localized on large plasmids, present in a low number of copies.

Cloning experiments with a 3 kb HindIII fragment cloned in a low copy number plasmid lead to a low production of toxins in a non-crystal-forming strain (cry$^-$) of *B. thuringiensis*. On the other hand, large quantities of toxins are synthesized when the gene is cloned in plasmids of high copy number (Arantes, O et al. 1991, Gene 108: 115–119).

SUMMARY OF THE INVENTION

The object of the invention is agents making it possible to obtain a high level of expression of the protein encoded in the cryIIIA gene and more generally agents making it possible to control the level of expression of DNA sequences coding for a specific protein of interest in bacterial strains, preferably Gram$^+$ strains such as Bacillus strains, since it is possible to obtain this expression when the coding DNA sequence is located on a vector, in particular on a plasmid of low copy number.

Generally speaking the invention relates to an expression system comprising a DNA sequence, able to intervene in the control of the expression of a coding nucleotide sequence and obtained by associating two distinct nucleotide sequences intervening in different but, preferably, not dissociable ways in the control of the expression of the coding sequence. The first nucleotide sequence exhibits a promoter activity whereas the second sequence, initiated by the promoter activity of the first, intervenes to enhance the expression of the gene. The DNA sequence of the invention makes it possible to attain a high level of expression of the coding part of a gene in a bacterium, in particular a Gram$^+$ type of bacterium.

The first nucleotide sequence of the expression system of the present invention identified in the framework of the present demand as being the promoter consists of either the promoter of the host strain in which the gene of interest to be expressed is introduced, or of an exogenous promoter, functional in the host used. The second nucleotide sequence of the expression system of the invention identified in the present application as being the "downstream region" designates any sequence preferably situated between the promoter and the sequence coding for a gene to be expressed, able to play a role particularly at the post-transcriptional level when the gene is expressed. More particularly, the downstream region does not act directly on the translation of the coding sequence to be expressed.

In a preferred manner, the "downstream region" consists of a nucleotide sequence, particularly an S2 sequence or a sequence analogous to S2, containing a region essentially complementary to the 3' end of the RNA, particularly the 16S RNA, of the ribosomes of bacteria, particularly of Gram$^+$ bacteria of the Bacillus type.

The nucleotides forming the DNA sequence according to the invention may or may not be consecutive in the sequence from which the DNA sequence is defined.

In the context of the present application the expression "DNA sequence able to intervene in the control of the expression of a coding nucleotide sequence" expresses the capacity of this DNA sequence to initiate or prevent the expression of the coding sequence or to regulate this expression in particular at the level of the quantity of the product expressed.

A DNA sequence according to the invention is such that the coding nucleotide sequence that it controls is placed immediately downstream, in phase with the same reading frame as it or, on the other hand, it is separated from this DNA sequence by a nucleotide fragment.

Hence the invention relates to a DNA sequence for the control of the expression of a coding sequence for a gene in a cell host, the DNA sequence is characterized in that it includes a promoter and a nucleotide sequence or downstream region situated in particular downstream of the promoter and upstream of said coding sequence. The nucleotide sequence or downstream region contains a region essentially complementary to the 3' end of a bacterial ribosomal RNA. The DNA sequence of the invention is capable of intervening to enhance the expression of the coding sequence placed downstream in a cell host.

The inventors have identified a DNA sequence of the type previously described, capable of intervening in the control of the expression of the coding sequence of the cryIIIA gene, and making it possible in particular to obtain a high level of expression when the coding sequence is placed on a low copy number plasmid.

The invention also relates to a DNA sequence characterized by the following properties:

- it is included in a DNA sequence about 1692 bp long, defined by the restriction sites HindIII-PstI ($H_2$–$P_1$ fragment), such as that obtained by partial digestion of the 6 kb BamHI fragment borne by the cryIIIA gene of *Bacillus thuringiensis* strain LM79;
- it is capable of intervening in the control of the expression of a coding nucleotide sequence placed downstream in a host cell, in particular a bacterial cell host of the *Bacillus thuringiensis* and/or *Bacillus subtilis* type.

The restriction sites referred to above are shown in FIG. 1.

In the remainder of the text the abbreviations $H_n$ will be used to designate the HindIII site having the position "n" with respect to the first HindIII site of the BamHI fragment. Similarly, the expression $P_n$ designates the PstI site at position "n" with respect to the first PstI site an the BamHI fragment.

The DNA sequence defined above can be isolated and purified for example from the plasmid bearing the cryIIIA gene of *Bacillus thuringiensis.*

The expression system for cryIIIA comprises a first nucleotide sequence or promoter situated between the TaqI and PacI sites (positions 907 to 990) and a second nucleotide sequence or "downstream region" included between the XmnI and TaqI sites (positions 1179 to 1559) as shown in FIG. 6. The presence of two sequences of this type is preferred to obtain an optimal level of expression of the cryIIIA gene or of another gene placed under the control of this expression system.

Also included in the framework of the invention is an expression vector characterized in that it is modified at one of its sites by a DNA sequence such as that described above so that said DNA sequence intervenes in the control of the expression of a specific coding nucleotide sequence.

A vector of the invention may preferably be a plasmid, for example a plasmid of the replicative type.

A particularly useful vector is the plasmid pHT7902'lacZ deposited with the CNCM (Collection Nationale de Cultures de Micro-organismes—Paris—France) on Apr. 20th 1993 under No. I-1301.

The object of the invention is also a recombinant cell host characterized in that it is modified by a DNA sequence such as that previously defined or by an expression vector described above. A particularly useful cell host is the strain 407-OA:Km$^R$ (pHT305P) deposited with the CNCM on May 3rd 1994 under No. I-1412.

DETAILED DESCRIPTION OF THE INVENTION

The object of the invention is a DNA sequence capable of influencing the expression of the coding part of a gene in a bacterial cell host. More particularly, the invention relates to the association of two nucleotide sequences, namely a promoter and a downstream region capable of intervening at the post-transcriptional level when the coding part of the gene is expressed.

The expression system of the invention which, as will be described in detail hereafter, probably involves the hybridization of a part of the downstream region with the 3' end of the 16S RNA of a bacterial ribosome, may be used for the expression of genes in a wide range of host cells. This extensive used of the expression system of the invention is possible, given the considerable homology observed at the level of the various 16S RNAs of bacterial ribosomes. Since the inventors have defined the regions essential for its functioning, the expression system of the present invention can thus be used in any type of bacterial host, the necessary adaptations forming part at the knowledge of the specialist.

In general and without wishing to restrict it for reasons which will become evident below, the expression system of the present invention when used for the expression of genes in Gram$^+$ bacteria of the Bacillus type is situated upstream from the coding part of the gene to be expressed. More particularly, the downstream region is normally situated immediately upstream from the gene whereas the promoter is located upstream from the downstream region, although another position might be envisaged for this latter. It is possible to envisage the displacement of the downstream region when the system is used in a cell host of the *E. coli* type in which the mRNAs are degraded in the reverse sense. It is also possible to envisage the use of a downstream region downstream and upstream of the coding sequence which would permit the "protection" of the coding region by a mechanism which will be described in detail below.

According to a first preferred embodiment of the invention, the DNA sequence corresponds to the HindIII-PstI ($H_2$–$P_1$) sequence described above and comprises two nucleotide sequences (a promoter and a downstream region) having distinct functions.

According to a particularly useful embodiment of the invention, the DNA sequence corresponds to the nucleotide sequence designated by the expression SEQ ID NO:1 and corresponding to the DNA fragment comprising the nucleotides 1 to 1692 of the sequence shown in FIG. 3.

The promoter and the downstream region of the DNA sequence of the invention are described in detail below.

Nucleotide Sequences Exhibiting a Promoter Activity

Preferably, a DNA sequence of the invention intervenes at the level of the control of transcription.

In this case it is a nucleotide sequence previously identified as being the promoter. Generally speaking as mentioned previously, the promoter is situated upstream from the downstream region and hence at a certain distance from the coding region of the gene. However, it is possible to envisage the relocation of the promoter provided it remains localized upstream from the downstream region.

As to the nature of the promoter, it seems preferable to use a promoter derived from the host cell used for the expression of the gene of interest. However, in certain situations the use of an exogenous promoter may be indicated. For example, promoters such as the promoters of the degO, λPL, lacZ, cryI, cryIV or α-amylene genes may be used.

In the context of the present invention particularly preferred fragments comprising a promoter region are the following fragments, shown in FIG. 1:

- the sequence defined by the TaqI-PacI restriction sites; for the sake of convenience, PacI is taken to designate the end of this fragment which is in reality found at nucleotide 990 of the sequence shown in FIG. 3, whereas the PacI site ends at position 985,
- or any fragment of this sequence, which conserves the properties of this sequence with respect to the control of the expression of coding nucleotide sequence.

More particularly, any part of at least 10 nucleotides of this sequence, naturally consecutive or not, capable of intervening in the control of the expression of a coding nucleotide sequence placed downstream in a cell host constitutes a preferred embodiment of the invention. For example, within the sequence mentioned previously are found the −35 (TTGCAA) and −10 (TAAGCT) boxes of the promoter.

According to another embodiment of the invention the "control" DNA sequences comprising the promoter mentioned above are characterized by their nucleotide sequence. In this respect, the object of the invention in particular is the DNA sequences corresponding to the following sequences:

- the DNA sequence corresponding to the SEQ ID NO:3 sequence, which corresponds to nucleotides 907 to 990 of the sequence shown in FIG. 3 (SEQ ID NO:1), or a variant comprising the nucleotides 907 to 985.

The object of the invention is also DNA sequences hybridizing under non-stringent conditions, such as those defined below, with one of the sequences described above. In this case, one of the above sequences in question is used as probe.

Sequences of the Downstream Region

A sequence of the invention included in the downstream region is selected for its capacity to intervene in order to enhance the expression of a gene which would be initiated by a promoter situated upstream from this sequence. It is probably a sequence capable of intervening at the post-transcriptional level when the coding sequence is expressed.

In fact, the experimental results obtained by the inventors seem to indicate that the post-transcriptional effect of the downstream region previously defined result, at least when the cryIIIA gene is being expressed, from the hybridization between the 16S ribosomal RNA of the host cell and an S2 sequence of the cryIIIA messenger RNA. It seems that the ribosome or a part of the ribosome binds to this downstream region and thus protects the mRNA from exonuclease degradation initiated at the 5'. This binding is thus expected to have the effect of increasing the stability of the messengers and of thus enhancing the level of expression of the cloned gene.

One of the particularly preferred fragments in the context of the embodiment of the invention and one which may be used as downstream region is the following fragment, shown in FIG. 1:

- the sequence defined by the restriction sites XmnI-TaqI (positions 1179 to 1556),
- or any fragment at this sequence conserving the properties of this sequence with respect to the control of the expression of a coding nucleotide sequence.

According to another embodiment of the invention, the "control" DNA sequences comprising the downstream region mentioned above are characterized by their nucleotide sequence. In this respect, the object of the invention is in particular the DNA sequences corresponding to the following sequences:

- the DNA sequence corresponding to the sequence SEQ ID NO:4, which corresponds to nucleotides 1179 to 1559 of the sequence shown in FIG. 3 (SEQ ID NO:1),
- the DNA sequence corresponding to the sequence SEQ ID NO:5, which corresponds to nucleotides 1179 to 1556 of the sequence shown in FIG. 3 (SEQ ID NO:1),
- the DNA sequence corresponding to the sequence SEQ ID NO:11, which corresponds to nucleotides 1413 to 1556 of the sequence shown in FIG. 3 (SEQ ID NO:1),
- the DNA sequence corresponding to the sequence SEQ ID NO:8, which corresponds to nucleotides 1413 to 1461 of the sequence shown in FIG. 3 (SEQ ID NO:1),
- the DNA sequence corresponding to the sequence SEQ ID NO:9 corresponding to the following DNA fragment:
  5'-AGCTTGAAAGGAGGGATGCCTAAAAACGAAGAACTGCA-3'
  3'-ACTTTCCTCCCTACGGATTTTTGCTTCTTG-5'
- the DNA sequence corresponding to the squence SEQ ID NO:10 corresponding to the following DNA fragment:
  5'-CTTGAAAGGAGGGATGCCTAAAAACGAAGAAC-3'
  3'-GAACTTTCCTCCCTACGGATTTTTGCTCTTG-5'

The object of the invention is also DNA sequences hybridizing, under non-stringent conditions such as those defined hereafter, with one of the sequences described above. In this case, the relevant sequence defined above is used as probe.

It seems that the downstream region consists initially of a region said to be "essential", sufficiently complementary to the 3' end of a 16S bacterial ribosomal RNA to allow the binding of the ribosome to this essential region. Downstream from this essential region bearing the ribosomal binding site, a second region is assumed to be situated comprising an additional structure capable of having an additional positive effect at the level of the expression of the coding sequence. It is possible that this second sequence prevents the movement of the ribosome once this latter is bound to the essential region.

For example, in the expression system of the cryIIIA gene, it seems that the nucleotide sequence situated between the positions 1413 and 1556 of the sequence shown in FIG. 3 comprises the region essential for ribosomal binding as well as the second region downstream from the binding site. Although the second region is not absolutely essential for obtaining an enhanced expression of the coding sequence, it seems that its deletion reduces the expression yields. In fact, experimental results have shown that the deletion of the region situated between the nucleotides 1462 and 1556 of the sequence shown in FIG. 3 leads to a slight diminution of the expression of the coding sequence.

It seems that the minimal length of the nucleotide sequence making possible adequate binding to the ribosome is about 10 nucleotides. The object of the invention is thus also any part of at least 10 nucleotides of the $H_2$–$P_1$ sequence, naturally or not consecutive, capable of controlling in a cell host of the Bacillus type the expression of a coding nucleotide sequence placed downstream or this part of the $H_2$–$P_1$ sequence.

In the specific case of the expression system of the cryIIIA gene, it would seem that the sequence of the "essential" region including the binding site is the following:

5'-GAAAGGAGG-3'

3'-CTTTCCTCC-5'

It is possible to make minor modifications at the binding site in as much as the intensity of the interaction between the 3' end of the 16S ribosomal RNA and this "essential" region is sufficiently strong for there to be hybridization between the ribosome and the binding site. From the calculations of the interaction energy which may be carried out by the specialist skilled in the art, modifications to the binding site can be envisaged if the intensity of the binding remains about the same as the the intensity measured when the natural "essential" region is used.

In the case of the binding site previously illustrated, it is possible to envisage certain modifications to the first four nucleotides as well as to the seventh nucleotide. However, it seems that the nucleotides in positions 5, 6, 8 and 9 are important for maintaining an appropriate intensity of interaction during hybridization with the 16S ribosomal RNA.

Since the 3' end of the 16S bacterial in RNA is relatively well conserved from one bacterial species to another, the expression system of the present invention may thus be used in a large number of bacterial hosts without substantial modifications having to be made.

The object of the invention is thus also a DNA sequence characterized by the following properties:

- it is contained in a nucleotide sequence hybridizing under non-stringent conditions with the DNA fragment included between the nucleotides 1413 and 1559 of the sequence shown in FIG. 3;
- it is capable of intervening in the control of the expression in a host cell of a coding sequence, in particular a sequence coding for a Bacillus polypeptide, toxic towards insects or a sequence coding for a polypeptide expressed during the stationary phase in Bacillus.

A sequence coding for a Bacillus polypeptide, toxic towards insect larvae is for example a sequence included in the cryIIIB gene of *B. thuringiensis.*

A DNA sequence corresponding to this definition can be identified by using oligonucleotide primers.

Hybridization under non-stringent conditions between the test DNA sequence and the DNA fragment included between the nucleotides 1413 and 1559 of the sequence of FIG. 3 used as will be conducted as follows:

The DNA probe and the sequences bound to the nitrocellulose filter or to the nylon filter are hybridized at 42° C. for 18 h with shaking in the presence of formamide (30%), 5×SSC of the 1×Denhardt solution. The 1×Denhardt solution is composed of 0.02% Ficoll, 0.02% polyyvinylpyrrolidone and 0.02% bovine serum albumin. The 1×SSC is composed of 0.15M NaCl and 0.015 M sodium citrate. After hybridization, the filter is succesively washed at 42° C. for 10 minutes in each of the following solutions:

formamide (30%), 5×SSC

2×SSC

1×SSC 0.5×SSC

The hybridization conditions just described are those which are used for all the applications of the present invention when necessary.

The DNA sequences according to the invention may be optionally recombinant among themselves or associated on a vector at different sites. In particular, the TaqI-PacI fragment is advantageously associated with the XmnI-TacI fragment with the sequence SEQ ID NO:8. Such sequences have the advantageous property of making possible a high level of expression (up to 60,000 Miller units) of the coding nucleotide sequence, a level of expression which may be observed with the beta-galactosidase gene.

Furthermore, particularly preferred fragments in the context of the embodiment of the invention are the following fragments shown in FIG. 8B:

- the sequence defined by the TaqI-TaqI restriction sites,
- or any fragment of these sequences conserving the properties of these sequences with respect to the control of the expression of a nucleotide coding sequence.

According to another embodiment of the invention, the DNA sequences referred to above are characterized by their nucleotide sequence. In this respect, the object of the invention is in particular the DNA sequences corresponding to the following sequences:

- the sequence SEQ ID NO:2, corresponding to the fragment comprising the nucleotides 907 to 1559 of the sequence shown in FIG. 3 (SEQ ID NO:1),
- the DNA sequence corresponding to the sequence SEQ ID NO:6, which corresponds to nucleotides 907 to 1353 (nucleotides 1 to 447 of SEQ ID NO:6) and 1413 to 1556 (nucleotides 448 to 591 of SEQ ID NO:6) of the sequence shown in FIG. 3 (SEQ ID NO:1),
- the DNA sequence corresponding to the sequence SEQ ID NO:7, which corresponds to nucleotides 907 to 990 (nucleotides 1 to 84 of SEQ ID NO:7) and 1179 to 1559 (nucleotides 85–465 of SEQ ID NO:7) of the sequence shown in FIG. 3 (SEQ ID NO:1).

The object of the invention is also DNA sequences hybridizing under non-stringent conditions such as those defined above with one of the sequences described above. In this case, one of the above sequences is used as probe.

The DNA sequences of the invention can be isolated and purified from Bacillus, in particular from *B. thuringiensis*; they can also be prepared by synthesis according to known procedures.

Also included in the framework of the invention are the RNA sequences corresponding to the DNA sequences described above.

The object of the invention is also a recombinant DNA sequence characterized in that it comprises a defined coding sequence under the control of a DNA sequence corresponding to one of the preceding specifications.

The capacity of the DNAs of the invention to intervene in the control of the expression of nucleotide sequences can be verified by implementing the following test:

- the DNA sequence of the invention whose capacity to intervene in the control of the expression of a coding sequence it is desired to evaluate is inserted in a low copy number plasmid upstream from a coding nucleotide sequence.
- the plasmid thus prepared is used to transform (for example by electroporation) a strain of *Bacillus thuringiensis*, for example a *B. thuringiensis* strain HD1 $cry^-$B;
- the Bacillus strain thus transformed is cultured under conditions permitting the expression of the coding nucleotide sequence;
- the expression product of this coding nucleotide sequence is detected by current qualitative and/or quantitative measuring procedures.

In order to carry out this test, the coding nucleotide sequence should advantageously be the coding sequence of the cryIIIA gene of *Bacillus thuringiensis* of for example a sequence coding for beta-galactosidase.

Cell Hosts

Different types a cell host may be used in the framework of the invention. Mention should be made as an example of Bacillus for example *Bacillus thuringiensis* or *Bacillus subtilis*. It is also possible to envisage the use of cells such as *E. coli*.

In cell hosts capable of sporulating, the coding sequence may be expressed during the vegetative phase or the stationary phase of growth or during sporulation.

A interesting cell host in the framework of the invention may also be constituted by a vegetal or animal cell.

If it is necessary or desired, depending on the nature of the coding nucleotide sequence expressed, a signal sequence can also be inserted in the expression vector of the invention so that the expression product of the coding sequence is exposed at the surface of the cell host, or even exported from this cell host.

In a really interesting manner it will be possible to use strains of Bacillus which have become asporogenic either naturally or as a result of mutation and in particular strains of *Bacillus subtilis* or *Bacillus thuringiensis.*

Since the inventors have demonstrated that the DNA sequences of the invention permit the expression of a defined coding sequence independently of the sporulation phase of strains of the Bacillus type, an asporogenic host may offer the advantage of providing agents of expression of coding sequences to be included in biopesticide compositions whose possible negative effects vis-a-vis the environment would be expected to be attenuated, and even eliminated.

The asporogenic host selected is particularly advantageous for expressing a coding sequence during its stationary phase of growth, when the coding sequence is under the control of one of the sequences of the invention.

In the case of asporogenic strains of Bacillus obtained by mutation, an example illustrating the particular efficacy of this type of strain for the expression of a coding sequence during the stationary phase of growth is the construction of a *B. thuringiensis* strain mutated in the spoOA gene. A *B. thuringiensis* strain in which the spoOA gene is inactivated and which bears a gene, for example a gene for an insecticidal toxin cryI, cryII, cryIII or cryIV or also a gene of industrial interest whose expression is placed under the control of the cryIIIA expression system offers advantageous characteristics. In particular, the *B. thuringiensis* strain 407.OA:Km$^R$ (pHT305P) whose construction is described in detail below has at least the following advantages:

a) overproduction of proteins during the stationary phase of growth;

b) the proteins (for example, biopesticides) remain enclosed in the cell and thus would be expected to have an increased persistence in the environment; and c) the potential problems linked to the dissemination of spores are thus avoided.

Other characteristics and advantages of the invention follow from the Examples which follow as well as from the Figures:

cri Bt is the replication region of the plasmid pHT1030 of *B. thuringiensis*

(B)—Simplified restriction map of the fragments bearing the cryIIIA gene. The A fragment is a 6 kb BamHI fragment of *B. thuringiensis* LM79; the restriction fragments G, P and H were obtained by partial digestion with HindIII and C was obtained after total digestion of fragment A with HindIII. These fragments were cloned in pHT304 to give the derivatives pHT305A, pHT305G, pHT305P, pHT305H and pHT305C, respectively. The cryIIIA gene (hatched box) and the direction of transcription are indicated. The numbers under each site indicate their order from left to right.

Figure 2:
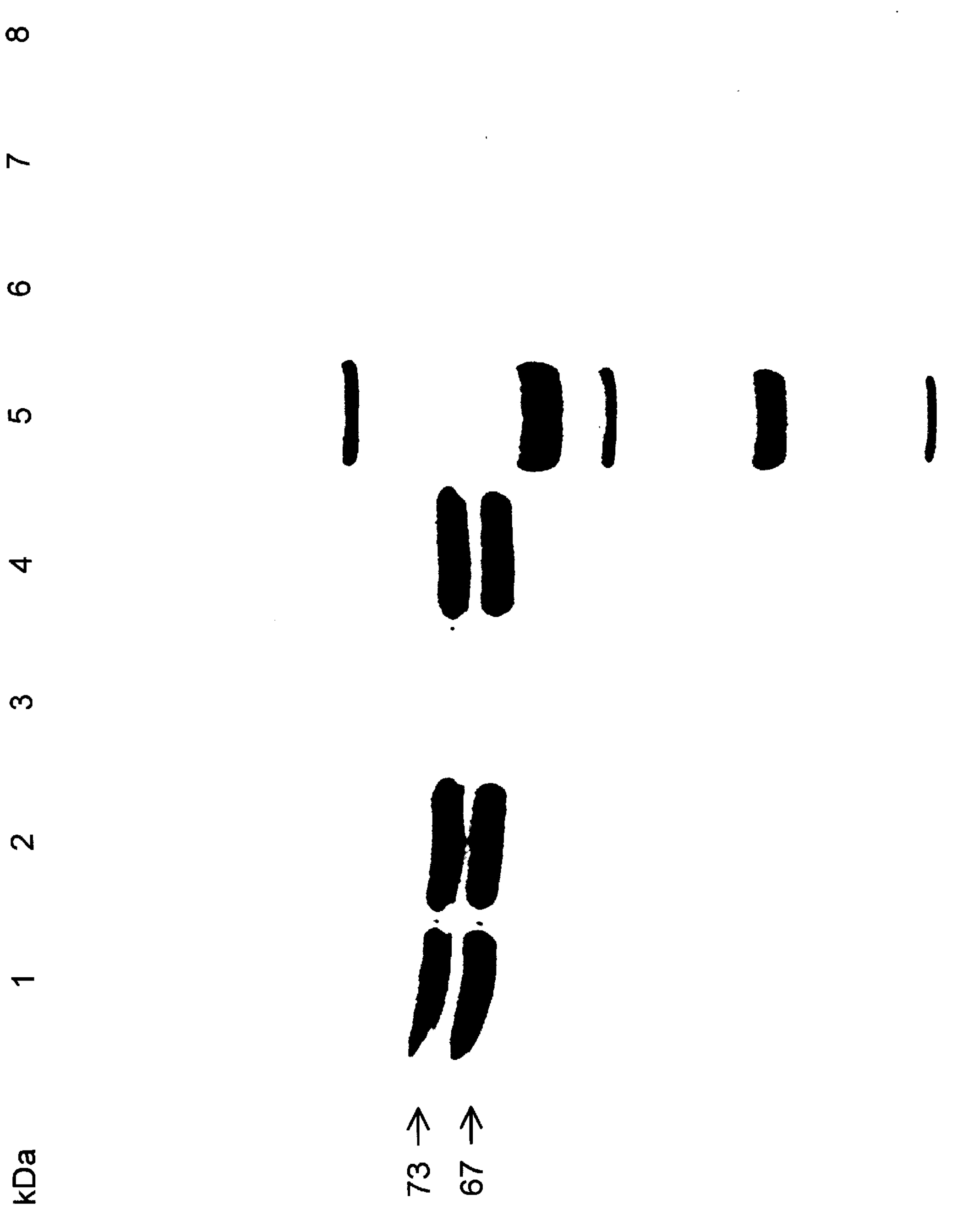

FIG. 2: Analysis of the proteins of the transformants of *B. thuringiensis* expressing the cryIIIA gene. An identical volume (20 $\mu$l) of samples was loaded into each well. The lines 1 to 4 and 6 to 8 of *B. thuringiensis* Kurstaki HD1 Cry$^-$ B bearing pHT305A, PHT305G, pHT305H, pHT305P, pH305HH$_2$-H$_3$, pHT305C and pHT304, respectively. Column 5 corresponds to the molecular weight markers (from top to bottom 97, 66, 60, 43 and 30 kDa). The arrows indicate the crystal components of 73 and 67 kDa.

Figure 3A:
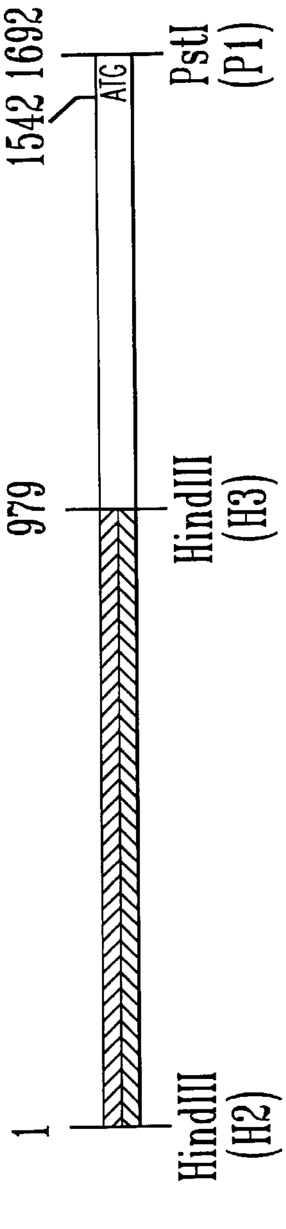

FIGS. 3A–C: Nucleotide sequence of the 5' end of the region upstream from the cryIIIA gene.

(A)—Physical map of the $H_2$–$P_1$ ($H_2$–$H_3$+$H_3$–P1) fragment in the 5' to 3' orientation. The positions at the nucleotides of the two HindIII sites ($H_2$+$H_3$) which define the grey tinted fragment are indicated. The second sequenced segment ($H_3$–$P_1$ fragment) was the fragment between the third HindIII site and the PstI site (P1). An ATG transcription initiation site for the CryIIIA toxin is shown. The numbering of the nucleotides is reported with respect to the sequenced fragment and not with respect to the initiation of transcription.

(B)—Nucleotide sequence of the fragment $H_2$–$_1$(SEQ ID NO:1). The ATG initiation codon is indicated in bold characters and the end of the major transcript on the gel, specific for the cryIIIA, corresponds to the T located at position 1413. Another transcript starts at nucleotide 983; it is apparently a minor component on the gel. The sequence comprises at least two inverted repeats. The numbering of the nucleotides starts from the second HindIII site and ends at the PstI site shown in FIG. 3A.

Figure 4:
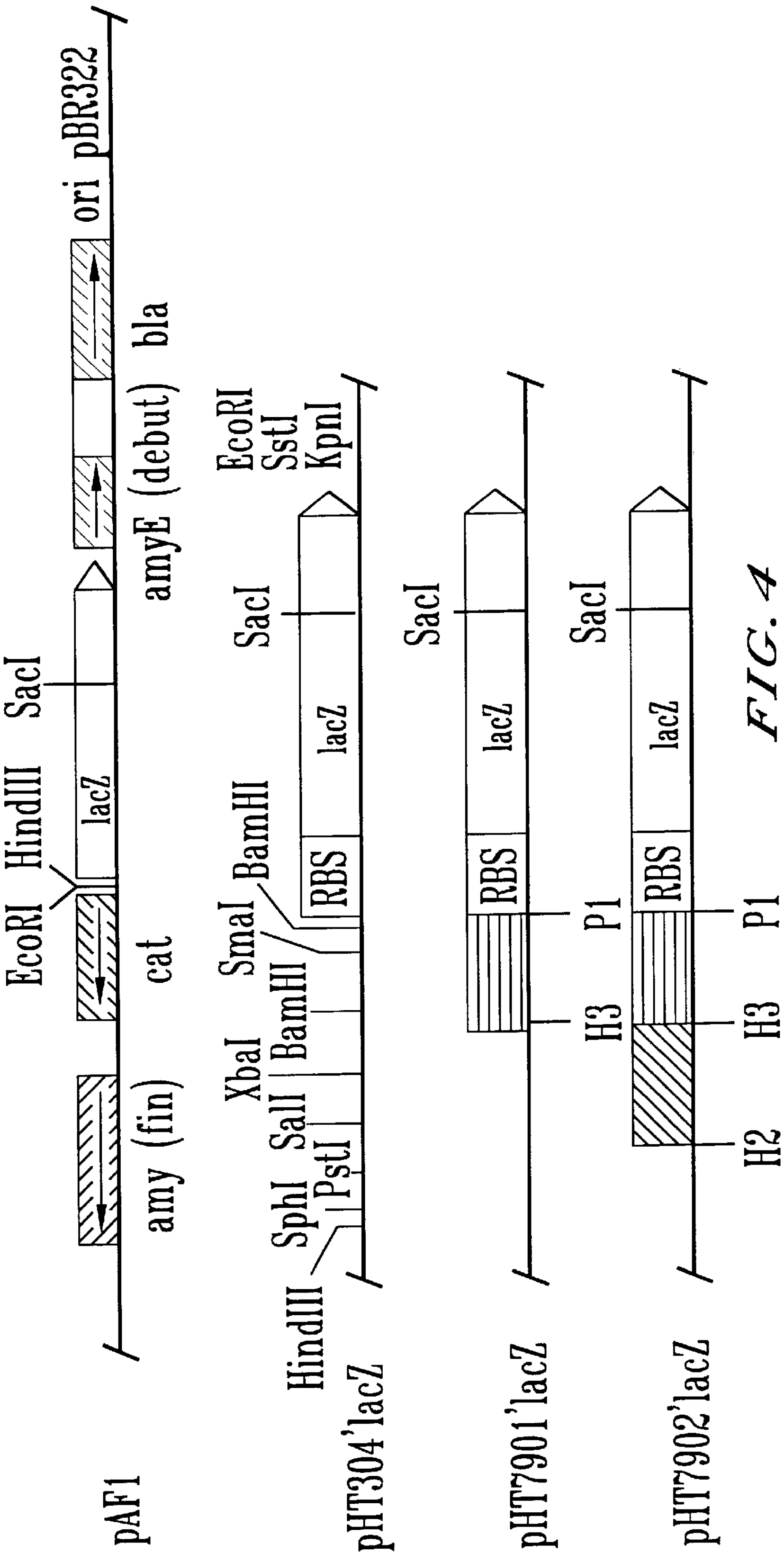

FIG. 4: Representation of the plasmids PAF1, pHT304'lacZ, pHT7901'lacZ and pHT7902'lacZ.

Figure 5:
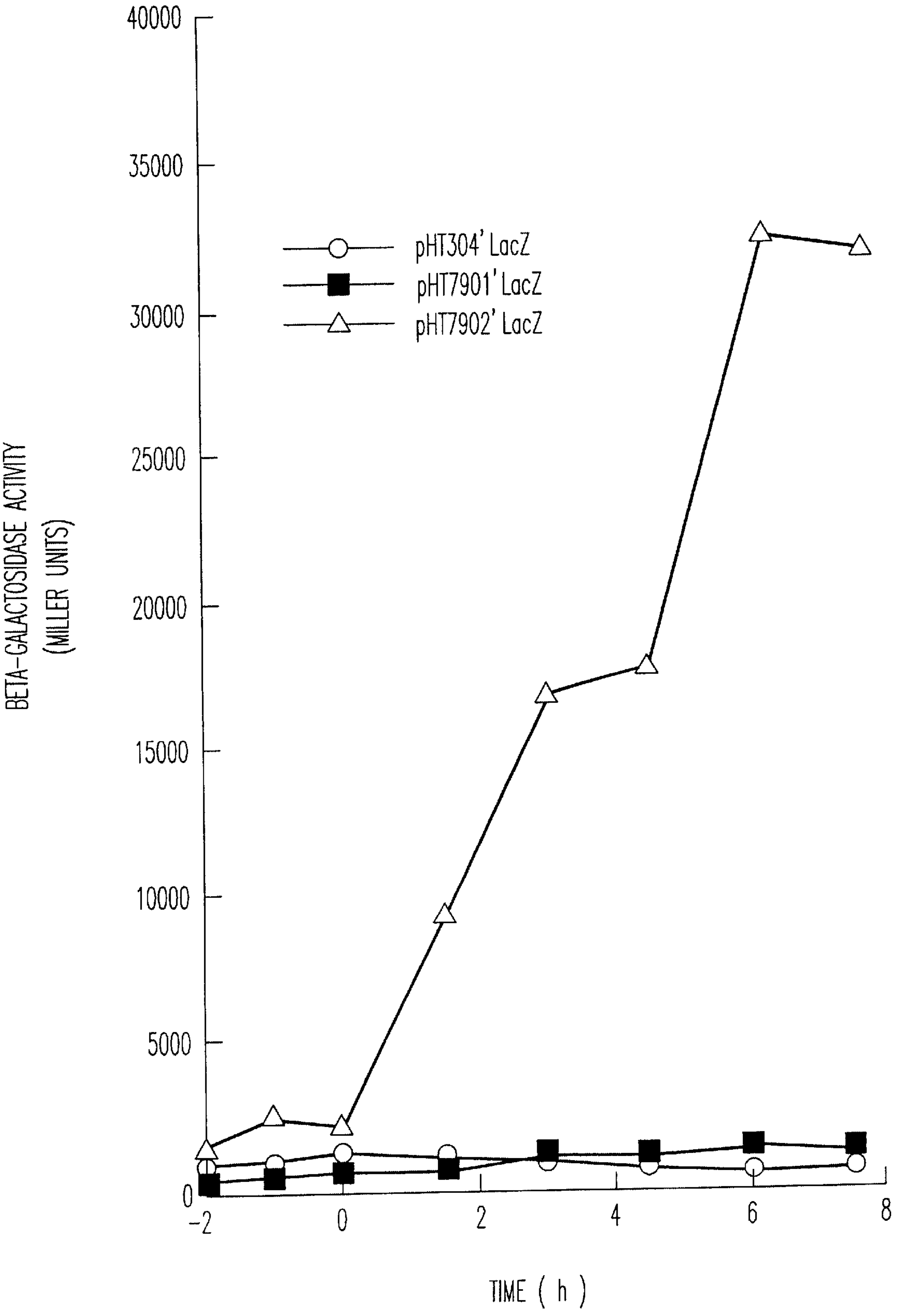

FIG. 5: Profile of beta-galactosidase activity. The growth of the Bt cells and the conditions for preparing the samples as well as the test are described in "Materials and Methods". the time $t_0$ indicates the end of the exponential phase and $t_n$ is the number of hours before (–) or after time zero.

Figure 6:
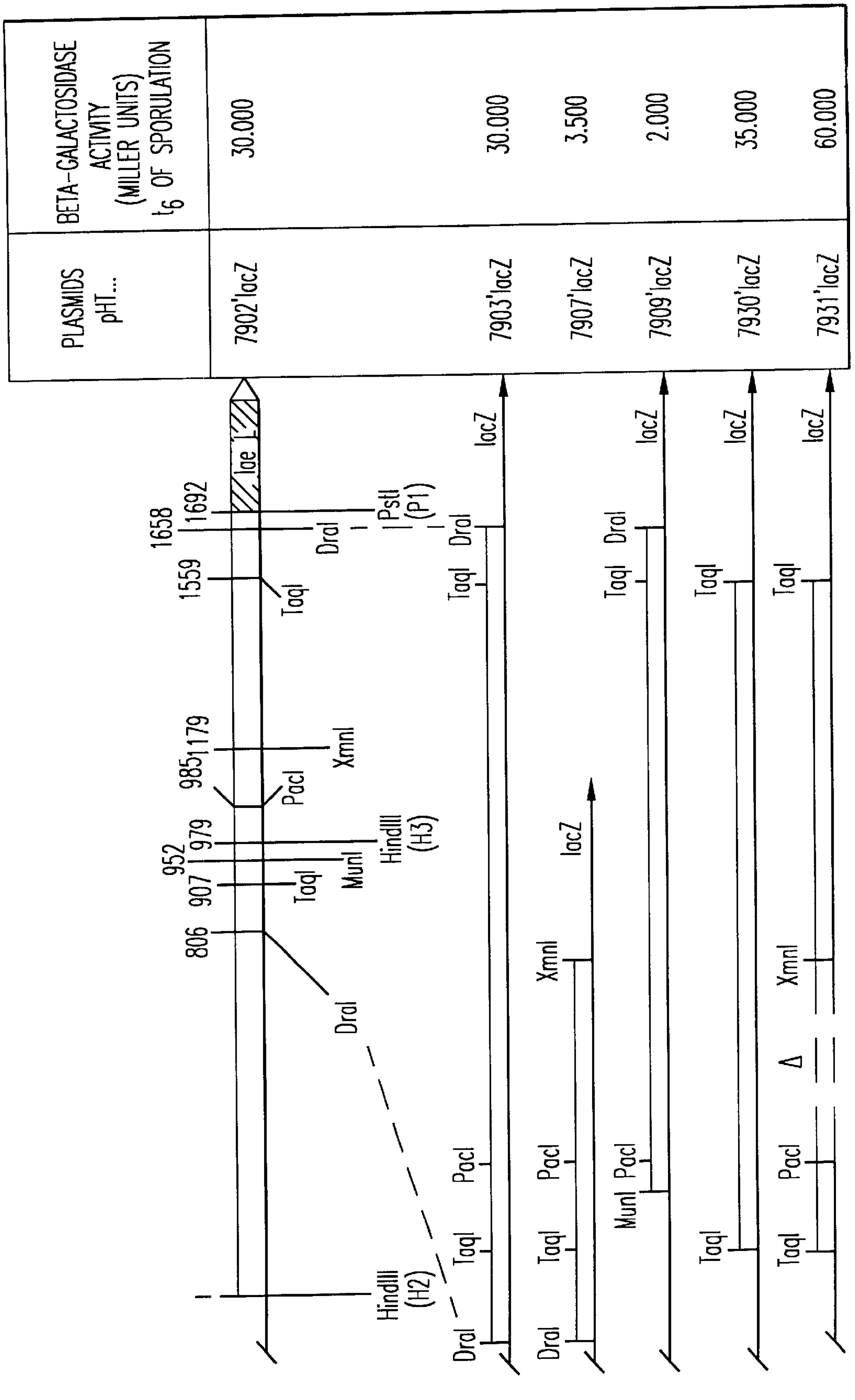

FIG. 6: Detailed restriction map of the plasmids pHT$_{7902}$'lacZ, 7903'lacZ, 7907'lacZ, 7909'lacZ, 7930'lacZ and 7931'lacZ. These plasmids were inserted into *B. thuringiensis* and the beta-galactosidase activity was measured at time $t_6$ of sporulation (in Miller units). The activities of 30,000, 30,000, 3.500, 2,000, 35,000 and 60,000 respectively are observed.

Figure 7:
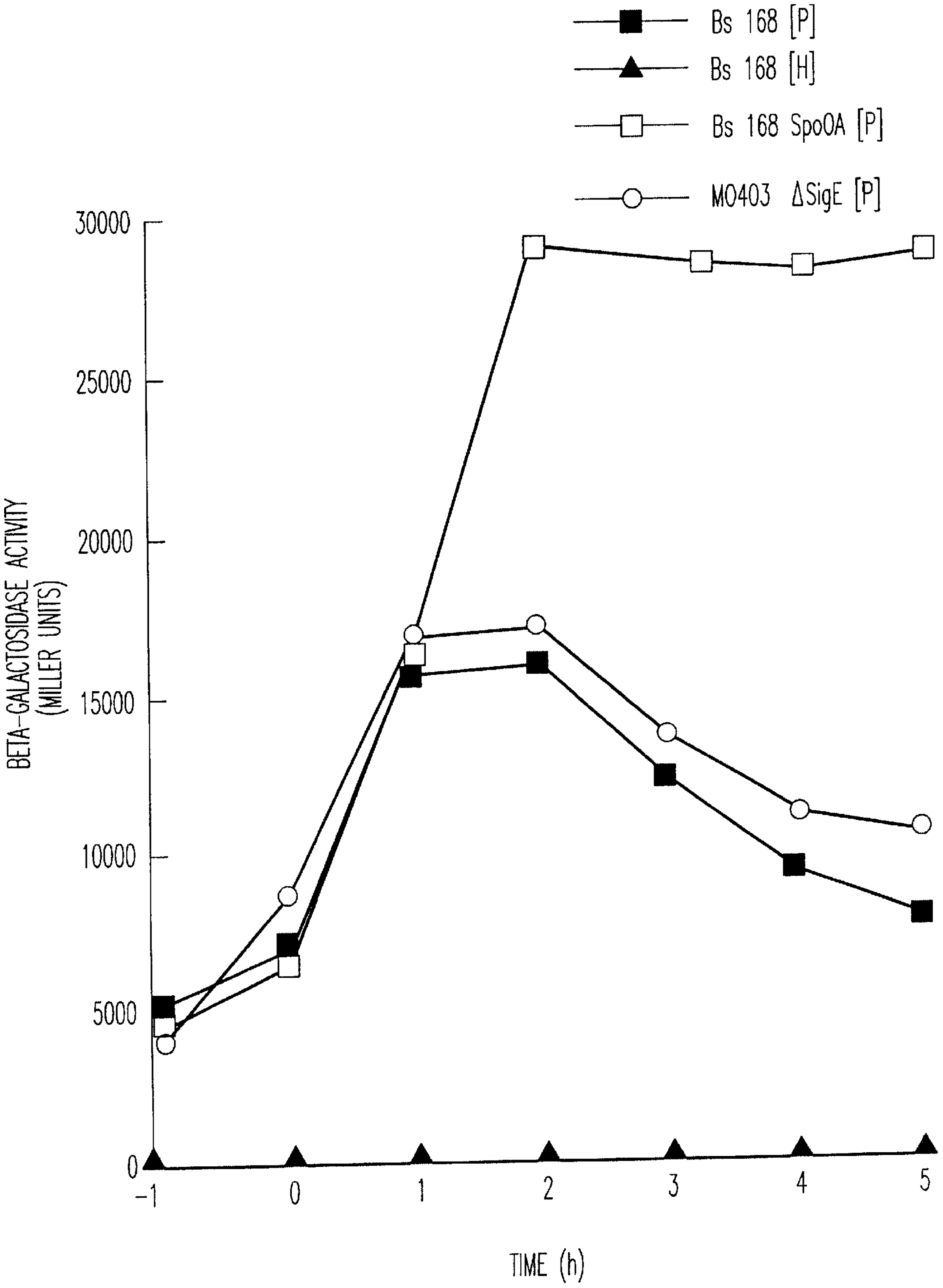

FIG. 7: Beta-galactosidase activity in *B. subtilis* strains Spo$^-$ and Spo$^+$; the cultures are grown in SP medium.

Figure 8A:
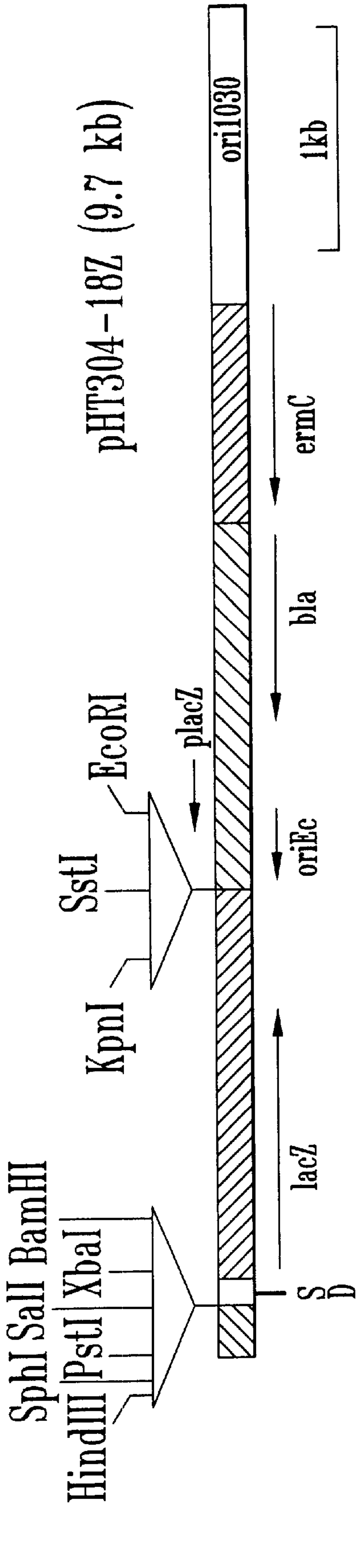
Figure 8B:
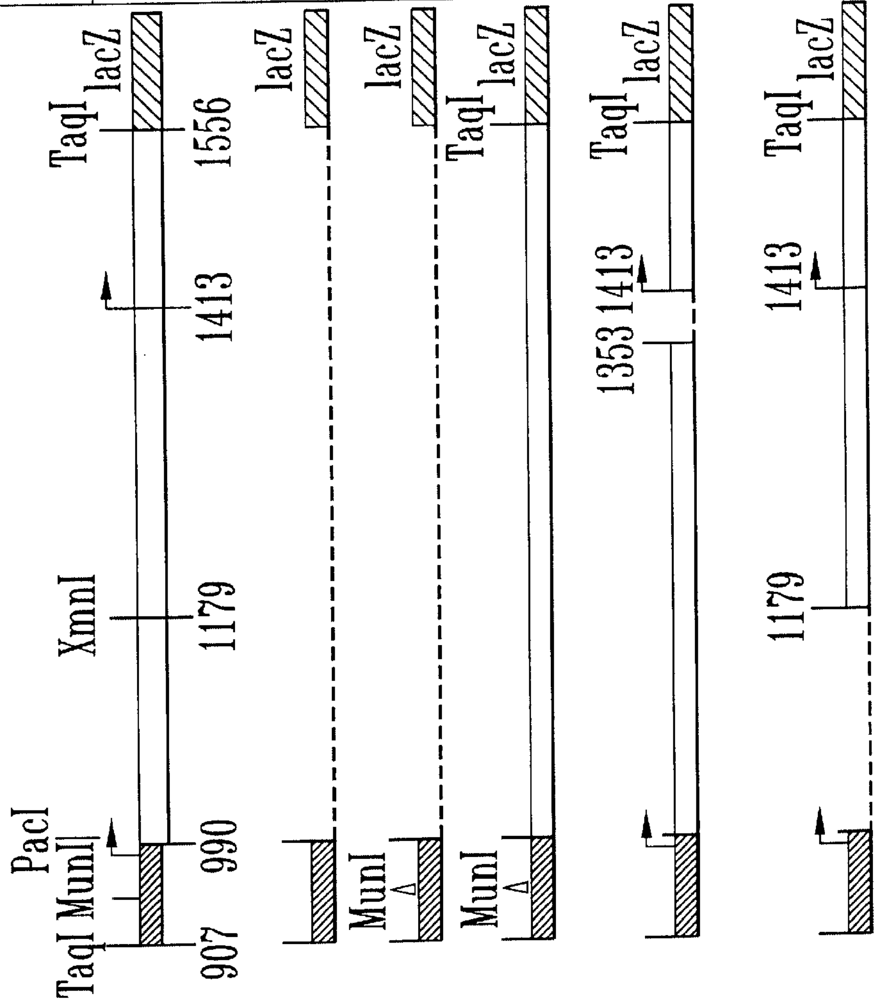

FIGS. 8A–B: Schematic restriction map of the constructions used to measured the transcriptional activity of the regions of the expression system of cryIIIA in *B. thuringiensis* strain kurstaki HD1 Cry$^-$B.

A—Physical map of the vector pHT304-18Z. The arrows indicate the direction of transcription of the genes ermC, bla, lacZ and the promoter placZ; and the orientation of the replication in *E. coli* (criEc). cri1030 indicates the region of replication of the plasmid pHT1030 (Lereclus and Arantes, Mol. Microbiaol. 1992, 7: 35–46). SD indicates the ribosomal binding site of the spoVG gene placed in front of the lacz gene (Perkins and Youngman, 1986, Proc. Natl. Acad. Sci. USA, 83: 140–144).

B—Physical representation and transcriptional activity of the different regions of the cryIIIA expression system fused with the lacZ gene. The numbering of the nucleotides is established according to the DNA sequence of the $H_2$–$P_1$ fragment presented in FIG. 3B. The arrows indicate the position of the 5' ends of the transcripts as they are identified by primer extension. The dotted lines indicate the localization of the deleted fragments. The beta-galactosidase activity of the different constructions was measured at times $t_0$ and $t_6$ of sporulation and is indicated in Miller units.

Figure 9:
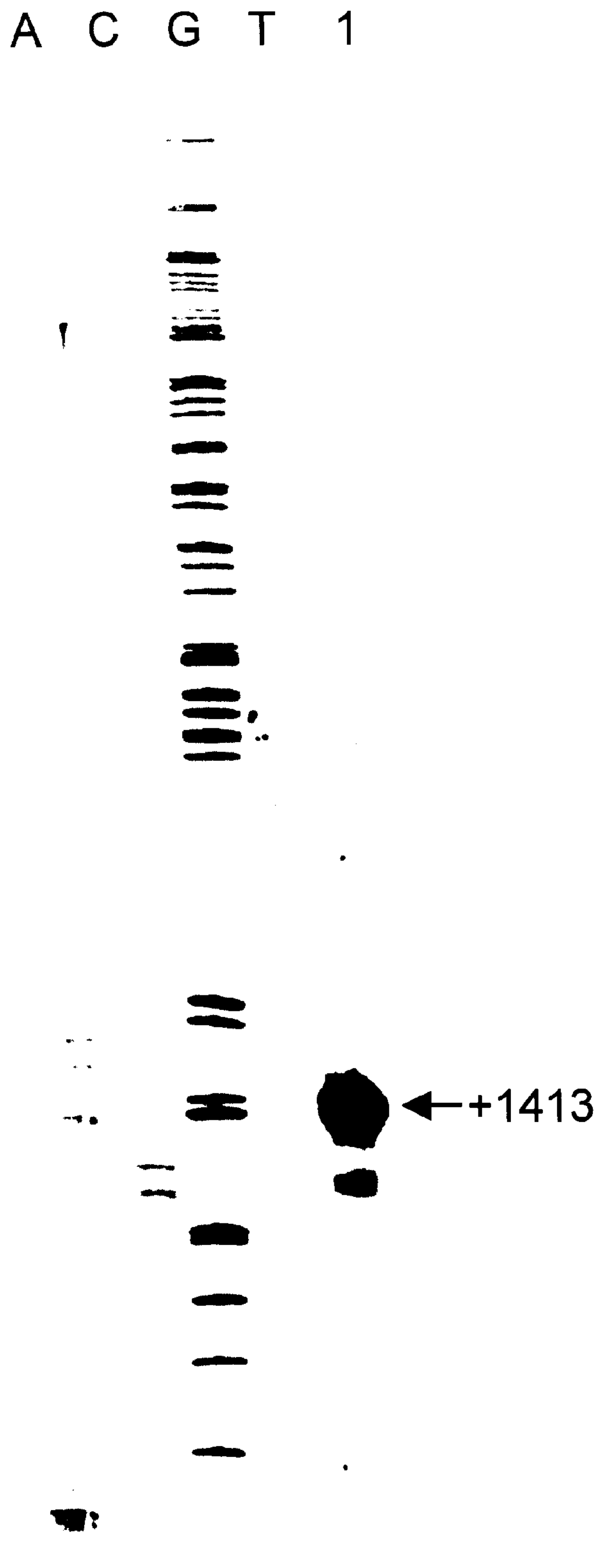

FIG. 9: Determination of the 5' end of the cryIIIA/lacZ transcript produced by the *B. thuringiensis* strain bearing the plasmid pHT7815/8'lacZ. The total RNA of the cells was extracted at $t_3$ and subjected to a primer extension experiment with the reverse transcriptase using as primer the following oligonucleotide (SEQ ID NO:12): 5'-CGTAATCTTACGTCAGTAACTTCCACAG>-3'. This oligonucleotide is complementary to the region localized between the ribosomal binding site of the spoVG gene and the initiation codon of the lacZ gene. The same oligonucleotide was used to determine the nucleotide sequence of the corresponding region of the plasmid pHT7815/8. The 5' end is numbered according to the DNA sequence of the $H_2$–$P_1$ fragment presented in FIG. 3B.

Figure 10:
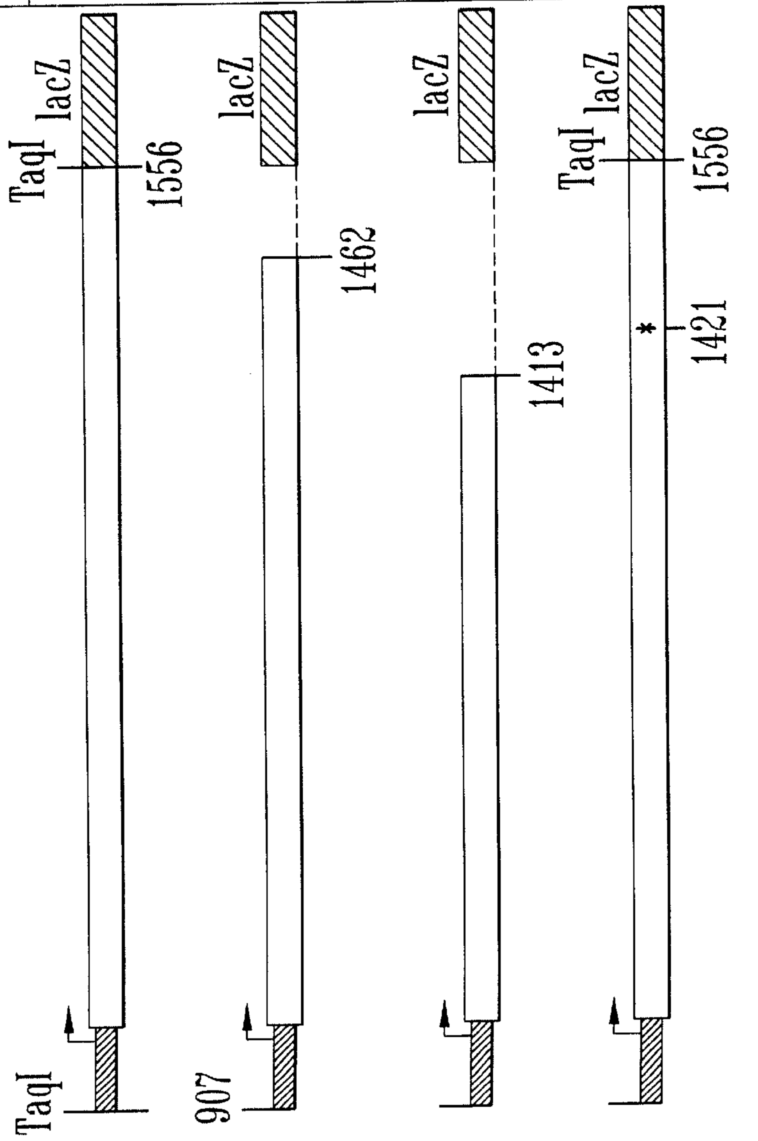

FIG. 10: Schematic physical map of the constructions used to measure the post-transcriptional activity of the downstream region of the cryIIIA expression system in *B. subtilis* strain 168. The numbering of the nucleotides is established according to the DNA sequence of the $H_2$–$P_1$ fragment presented in FIG. 3B. The arrow indicates the starting position of transcription located at position +984. The asterisk at position 1421 indicates the replacement of GGA by CCC. The dashed lines indicate the location of the deleted DNA fragments. The beta-galactosidase activity of the different constructions was measured at the time $t_3$ of sporulation and is indicated in Miller units.

Figure 11A:
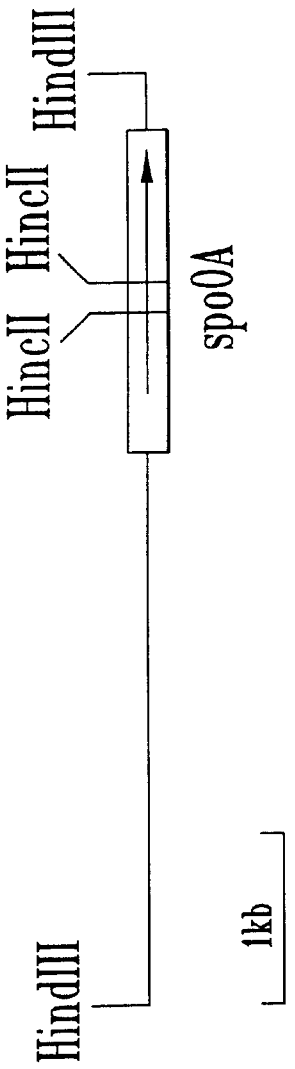

FIGS. 11A–B: Nucleotide sequence of the spoOA gene of *B. thuringiensis* strain 407.

A—Schematic restriction map of the 2.4 kb DNA fragment bearing the spoOA gene. The arrow indicates the orientation of the transcription of the spOA gene.

B—Nucleotide sequence of the open reading frame comprising the coding sequence of the spoOA gene (SEQ ID NO:16). The initiation codon GTG is indicated in bold characters. The two HincII sites are underlined. The three dots represent the stop codon.

MATERIALS AND METHODS

BACTERIAL STRAINS AND GROWTH CONDITIONS

*Escherichia coli* K-12 TG1 {Δ(lac-proAB) supE thi hdsD (F traD36 proA$^+$ proB$^+$ lacIq lacZΔM15)} Gibson, T. J. et al. 1984 Thesis, University of Cambridge, Cambridge was used as host for the construction of the plasmids represented in FIG. 1B and for the bacteriophage M13.

*E. coli* MC1061 {hsdR mcrB araD139Δ (araABC-leu) 7679 Δ lacX74 galU galK rpsL thi} (Meissner, P. S. et al., 1987 Proc. Natl. Acad. Sci. USA 84: 4171–4175) was used as host for the construction of the plasmids shown in FIG. 7.

*B. thuringiensis* strain LM 79 which contains the cryIIIA gene was isolated and characterized by Chaufaux J. et al. 1991. INRA colloquia 58: 317–324.

This strain belongs to the serotype 8 and produces quantities of toxins similar to those produced by other strains of *B. thuringiensis* bearing the cryIIIA gene (Donovan, V. P. et al. 1988 Mol. Gen. Genet. 214, 365–372—Sekar, V. et al. 1987 Proc. Natl. Acad Sci. USA 84: 7036–7040).

*B. thuringiensis* of the subspecies Kurstaki HD1 Cry$^-$B was used as host for the studies of regulation of the cryIIIA gene. The *E. coli* strains were cultured at 37° C. in a Luria medium and transformed according to the method described by Lederberg and Cohen (1974 Bacteriol. 119: 1072–1074).

The *B. thuringiensis* strain subspecies Kurstaki HD1 Cry$^-$B was cultured and transformed by electroporation according to the procedure described by Lereclus et al. (1989 FEMS Microbiol. Lett. 60: 211–218).

The antibiotic concentrations for the selection of the bacteria were 100 μg/ml for ampicillin and 25 μg/ml for erythromycin.

Construction of the Plasmids

Figures 1A, 1B:
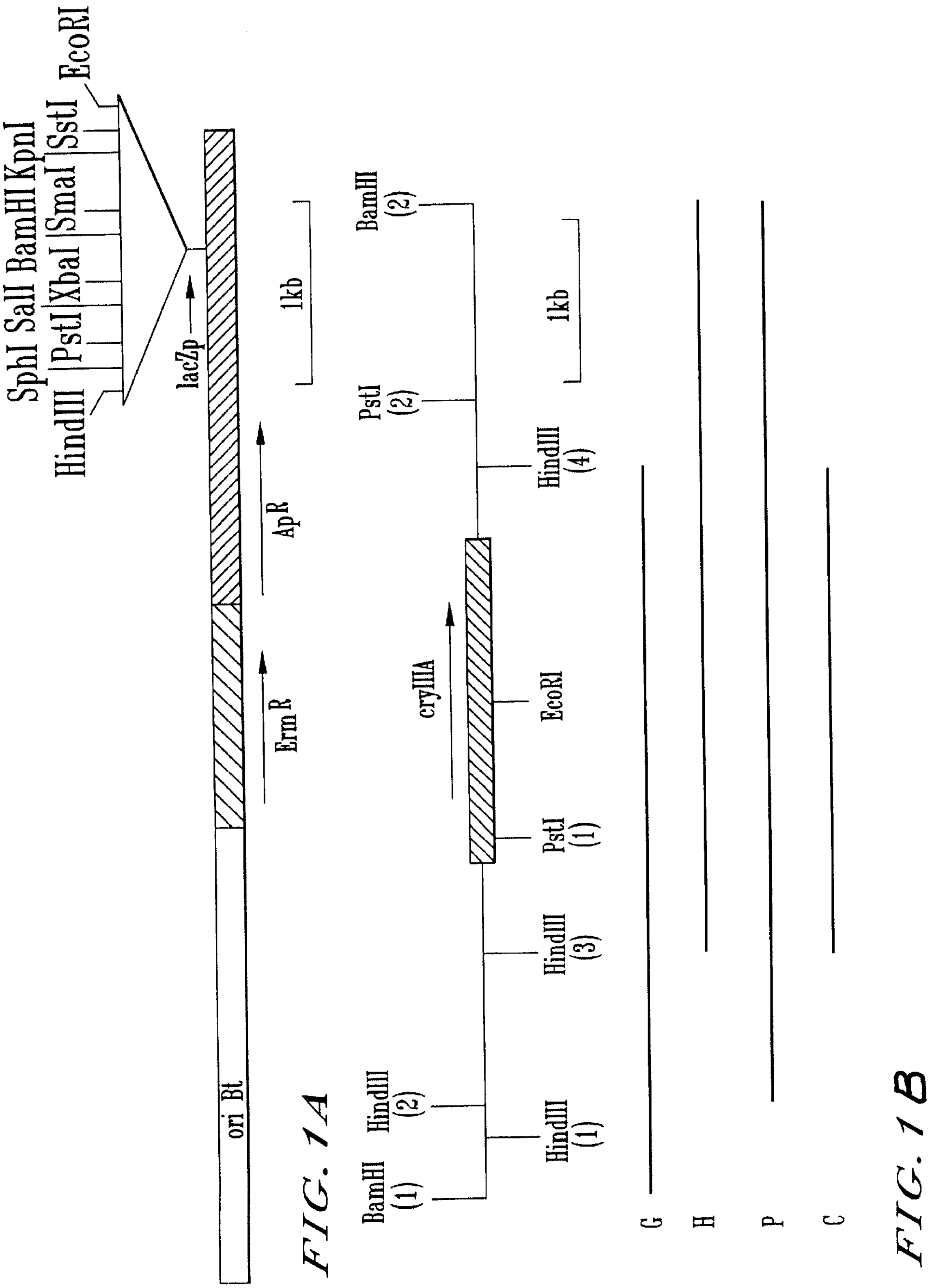
FIGS. 1A–B: Schematic restriction map of the plasmids used (A)—Physical map of the shuttle vector pHT304. The arrows above Erm$^R$ and Ap$^R$ indicate the direction of transcription of the ermC and bla genes, respectively. The arrow and the expression LacZ indicate the direction of transcription from the promoter of the LacZ gene.

The 6 kb BamHI fragment bearing the cryIIIA gene and the adjacent regions was isolated from *B. thuringiensis* LM79 and inserted into the unique BamHI site of pUC19 to produce pHT791 which was employed as DNA source for the construction of the various plasmids used here. The plasmid pHT305A was obtained by insertion of the 6 kb BamHI fragment into the unique BamHI site a the shuttle vector pHT304 (Arantes, O and Lereclus D 1991, Gene 108: 115–119) (FIG. 1A). Samples of the 6 kb BamHI fragment were partially or completely digested with HindIII and the resulting fragments were cloned between the BamHI and HindIII sites or at the HindIII site of pHT304 to give the derivatives $pH_{1305}G$, pHT305H, $pH_{1305}P$ and pHT305C (FIG. 1). The plasmid $pHT305H\Omega H_2H_3$ was obtained by inserting the $H_2$-$H_3$ fragment filled at the ends in the SmaI site of $pHH_{305}H$ (fragment defined respectively by the second and third HindIII sites of the 6 kb fragment).

The 4.5 kb SmaI-KpnI fragment a the pTV32 plasmid (Perkins, J. B. et al; 1986 Proc. Natl. Acad. Sci. USA 83: 140–144) containing the lacZ and ermC genes was cloned in pEB111 (Leonhardt, H. et al. 1988 J. Gen. Microbiol.134: 605–609) to give the plasmid pMC11. The plasmid pHT304'lacZ used to construct the transcriptional fusions was obtained y cloning the 3.2 kb DraI-SmaI restriction fragment containing the lacZ gene lacking a promoter isolated from pMC11, at the unique SmaI site of pHT304. The plasmid pHT7901'lacZ was obtained by cloning the $H_3$–$P_1$ fragment [(HindIII-PstI) see FIG. 3A] between the unique HindIII and PstI sites of pHT304'lacZ. The plasmid pHT7902'lacZ was constructed by cloning the $H_2$–$H_3$ fragment (FIG. 3A) into the unique HindIII site of phT7901'lacZ. The orientation of the $H_2$–$H_3$ fragment was determined by mapping the HpaI and BalI restriction sites with respect to the PstI site. Two HpaI sites are located at the nucleotide positions of 50 and 392; the BalI site is located at nucleotide position 670 (FIG. 3). The general structure of the recombinant plasmids bearing the lacZ fusion is given in FIG. 4.

DNA Manipulations

The standard procedures were used to extract the plasmids from *E.coli* to transfect the recombinant DNA of phage M13 and to purify the single-stranded DNA (Sambrook J et al., 1989 A laboratory manual, $2^{nd}$ ed. Cold Spring Harbor Laboratory -Cold Spring Harbor, N.Y.). The restriction enzymes, the T4 DNA ligase and the T4 polynucleotide kinase were used in accordance with the manufacturer's instructions. The Klenow fragment of the DNA polymerase I and deoxyribonucleoside triphosphates were used to provide the $H_2$-$H_3$ fragment with blunt ends. The DNA restriction fragments were purified on agarose gels using the PREP A GENE kit (Bio-Rad). The nucleotide sequences were determined by the dideoxy chain termination method (Sanger F. et al. 1977 Proc. Natl. Acad. Sci. vol. 175, 1993 USA 74: 5463–5467) using the M13mp18 and M13mp19 phages as matrices as well as the SEQUENASE kit version 2.0 (US Biochemical Cor. Cleveland Ohio) and {$\alpha$-$^{35}$S} dATP (15 TBq; Amersham, United Kingdom).

Computer Analysis

The DNA sequences were analysed by using the programs a the Pasteur Institute on a general data-processing computer MV10000.

Extraction of the RNA Extension of the Primers, Northern Analysis of the RNA and Dot Blot Analysis.

The *B. thuringiensis* subspecies Kurstaki HD1 Cry$^-$B (pHT305P) was cultured in a HCT medium (Lecadet et al. 1980 J. Gen. Microbiol. 121:203–212) at 30° C. by shaking. The samples were taken at $t_0$, $t_3$, $t_6$ and $t_9$ ($t_0$ is defined as being the start of sporulation and tn indicates the number of hours after the start of sporulation). The cells were recovered by centrifugation, resuspended in a HCO medium (Lecadet, M. M. et al., 1980 J. Gen Microbiol. 121: 203–212) containing 50 mM of sodium azide and immediately frozen at −70° C. until the RNA was extracted (Glatron, M. F. et al., 1972, Biochemie 54: 1291–1301). For the elongation test of the primer, a first oligonucleotide (SEQ ID NO:13)—a 39-mer (3'-CTT AGG CTT GTT AGC TTC ACT TGT ACT ATG TTA TTT TTG-5') complementary to the region 3'—1544 to 1583—5' of the cryIIIA gene was synthesized and its 5' end was labelled with {$\gamma$-32P} dATP (110 TBq/mmol) by the T4 polynucleotide kinase. The 39-mer oligonucleotide was purified on a column of Sephadex G-25 (Pharmacia) (incorporation about 70%) and to be used as primer it was mixed with 50 $\mu$g of total RNA.

A second oligonucleotide, a 32-mer complementary to the region located between the positions 1090 and 1121 was also used as primer and made possible the detection of a second transcript, the start of transcription of which is situated at position 983. This oligonucleotide corresponds to the sequence

5'-GTTAGATAAGCATTTGAGGTAGAGTCCGTCCG-3' (SEQ ID NO:14)

The hybridization (at 30° C.), the extension of the primer and the analysis of the products were carried out as described by Debarbouillé, M et al., (1983, J. Bacteriol. 153: 1221–1227). The primers of the 39-mer and the 32-mer were used for the elongation of the fragment $H_3$–$P_1$ cloned in M13mp19 and for the elongation of the $H_2$–$P_1$ fragment cloned in pHT7902'lacZ, respectively. The products resulting from the reactions were placed on gels in parallel with transcription products to determine the 5' ends of the transcripts.

A Northern blot analysis was performed with denatured RNA fractionated by electrophoresis on agarose gels containing 1.5% formaldehyde and transferred in a vacuum to HYBOND-N$^+$ (Amersham) membranes in 20×SSC for 1 h (1×SSC corresponds to 150 mM NaCl plus 15 mM sodium citrate, pH 7.0). The Pst I-EcoRI restriction fragment of 874 bp (internal to the cryIIIA gene) was labelled with $^{32}$P with a nick translation kit (Boehringer Mannheim), then denatured and used as probe. A prehybridization was performed at 42° C. for 4 hours in a medium containing 50% formamide-1M NaCl-1% sodium dodecyl sulfate (SDS)—10×Denhardt's solution-50 mM Tris HCl (pH 7.5)-0.1% sodium PP, denatured salmon sperm DNA (>100 $\mu$g/ml) and the labelled probe ($10^8$ cpm/$\mu$g) was added to the prehybridization solution and the incubation was continued overnight. The membrane was washed at 65° C. for 30 minutes twice with 2×SSC-0.5% SDS, once with 2×SSC-0.5% SDS, and once with 0.5×SSC-0.5% SDS.

Equal quantities of RNA of synchronous cultures of B. Thuringiensis subspecies Kurstaki HD1 Cry$^-$B bearing the plasmids pHT305P or pHT305H taken at $t_3$ were deposited on to HYBOND-C Extra membranes (Amersham) with a manifold apparatus (Schleicher & Schueller) by using the dot blot protocol described by Sambrook et al. (Sambrook, J. et al. 1989 Cold Spring Harbor Laboratory, Cold Spring Harbor, N.Y.). The probe and the hybridization conditions were those described in the Northern blot tests.

Preparation of the Crystal and Analysis

The cells were cultured in a HCT medium at 30° C. with shaking for 48 hours and the crystals were prepared according to the method described in the publication by Lecadet, M. M. et al. (1992 Appl. Environ. Microbiol. 58: 840–849) with the exception of the fact that the NaCl concentration was 150 mM. For gel electrophoresis on polyacrylamide-SDS (PAGE) 20 $\mu$l of each sample were used (Lereclus, D. et al. 1989 (FEMS Microbiol. Lett. 66 : 211–218).

Test for the Detection of Beta-galactosidase

The strains of *E. coli* and *B. thuringiensis* containing the lacZ transcription fusions were detected by depositing on the solid medium the chromogenic substrate 5-brmo-4-chloro-3-indolyl-β-D-galactopyranoside (X-Gal) (40 $\mu$g/ml) and suitable antibiotics. The isolated strains were cultured as indicated and recovered at $t_{-2}$, $t_1$, $t_0$, $t_{1.5}$, $t_3$, $t_{4.5}$, $t_6$ and $t_{7.5}$. After centrifugation, the pellets were immediately frozen at −70° C. (in order to prevent the inactivation of the beta-galactosidase) and thawed just before the treatment with ultrasonics to detect the beta-galactosidase (Msadek, T. et al. 1990 J. Bacteriol. 172: 824–834). The specific activities presented (expressed in Miller units per milligram of protein) correspond to the mean values of at least two independent experiments.

RESULTS

The Expression of the CryIIIA Gene Requires the Presence of a DNA Fragment Upstream From the Gene.

Arantes and Lereclus (1991 Gene 108: 115–119) have shown that the cryIIIA gene was only weakly, expressed in the *B. thuringiensis* strain HD1 Cry$^-$B when it was cloned in a low copy number vector such as pHT304 (4 copies per chromosome equivalent).

Starting from a 6 kb BamHI fragment bearing the cryIIIA gene and the adjacent regions (FIG. 1B) isolated from the *B. thuringiensis* strain LM79 specific for the Coleoptera, it has been investigated whether regions upstream from the gene might be implicated in the regulation of the expression d this gene. The 6 kb fragment was cloned into the unique BamHI site of the vector pHT304 (FIG. 1A); fragments obtained after partial or total digestion by HindIII of the 6 kb BamHI fragment were also inserted independently in the same plasmid to give the derivatives pHT305A, pHT305G, pHT305H, pHT305P and pHT305C (FIG. 1B). The five recombinant plasmids were then introduced in *B. thuring-*

*iensis* subspecies Kurstaki HD1 $Cry^{-}B$ by electroporation and the transformants were cultured for two days at 30° C. in a HCT medium (Lecadet, M. M. et al. 1980 J. Gen. Microbiol. 121: 203–212) containing 25 μg of erythromycin per ml.

Preparations of spores containing crystals were recovered from cultures and examined by phase contrast microscopy and SDS-PAGE (FIG. 2). The recombinant strains bearing the vectors pHT305A, pHT305G and pHT305P (FIG. 2, lines 1, 2 and 4 respectively) produced large quantities of a flat rhomboid crystal characteristic of strains active against the larvae of the Coleoptera, The principal components at these crystals were two peptides of about 73 and 67 kDa such as those previously described for the *B. thuringiensis* strains bearing cryIIIA (Donvan, W. P. et al. 1988 Mol. Gen. Genet. 214: 365–372).

On the other hand, no production of crystal was detected with the strains bearing pHT1305H or pHT305C (FIG. 2, lines 3 and 7 respectively). The hypothesis has been put forward that these plasmids lack certain elements present, conversely, in the derivatives pHT305A, pHT305G and pHT305P. This possible additional element is situated ona 1 kb DNA fragment between the second and third HindIII site, this fragment being designated by $H_2$–$H_3$ (FIG. 1B). In order to test whether its activating effect depended on its position, the $H_2$–$H_3$ fragment was ligated to a SmaI site of pHT305H. In the resulting plasmid (pHT305HΩ$H_2H_3$), the $H_2H_3$ plasmid is located downstream from the cryIIIA gene. The synthesis of the CryIIIA toxin of pHT305HΩ$H_2H_3$ proved to be as weak as with the plasmid pHT305H (FIG. 2, line 6). This absence of effect might be due to either the new location of the $H_2$–$H_3$ fragment, this location being inappropriate or to the disorganization of its functional structure. In this case, the functional element starting within the $H_2$–$H_3$ fragment would be extended to a region beyond the HindIII site described and would potentially comprise the region of the promoter.

Sequencing of the DNA and Analysis

The nucleotide sequence of the 979 1 $H_2$–$H_3$ fragment of the plasmid pHT791 was determined (FIG. 3B). Furthermore, the sequence of 713 bp extending from the third HindIII site to the first PstI site ($H_3$–$P_1$ fragment) was determined (FIG. 3B). This second fragment bears the region upstream of the promoter, the promoter itself, the potential ribosomal binding site and the first 151 codons of the cryIIIA gene (Sekar, V et al., 1987 Proc. Natl; Acad. Sci. USA 84: 7036–7040). There is no difference between the sequence of the $H_3$–$P_1$ fragment isolated from the strain LM79 and the corresponding regions of the cryIIIA genes isolated from *B. thuringiensis* subspecies tenebrionis, *B. thuringiensis* subspecies san diego and the strain EG2158 (Donovan W. P. et al., Herrnstadt C. et al., Höfte H. J. et al., Sekar V. et al.). No sequence potentially coding for a protein other than that corresponding to the 5' end of cryIIIA was found. This region exhibits a high proportion of A+T bases (adenine-plus-thymine) corresponding to about 81% between the bases 770 and 990 and two inverted repeat sequence. The first inverted repeat sequence is imperfect (16 of the 17 bp are identical) with a centre of symmetry at nucleotide 858 and the second is a perfect inverted repeat of 12 bp with a centre at symmetry at nucleotide 1379. The free energies leading to the formation d the stem loop structures calculated according to the method of Tinoco et al. (Tinoco, J. J. et al., 1973 Nature (London) New Biol. 246: 40–41) were −57.7 and −66.1 kJ/mol., respectively.

Analysis of the Initiation Site and the Duration of Transcription the Presence of the $H_2$–$H_3$ Fragment.

Sekar et al. have mapped the initiation site of the transcription of the cryIIIA gene starting from the RNAs isolated from early phase cells (stage II) and intermediary phase cells (stages III to IV) of sporulation by using the mung bean nuclease. These periods of growth correspond to $t_2$ to $t_5$. The extension from the primers was performed con RNAs extracted from cells in culture at $t_0$, $t_3$, $t_6$ and $t_9$ to determine whether other initiation sites are involved during the early and late phases of growth and in corder to determine at which stage maximal transcription occurs. A start site for transcription appeared in the form of a weakly radioactive signal in the samples taken at $t_0$ and $t_9$ and this signal proved to be more intense in the samples at $t_3$ and $t_6$. This initiation site of transcription was mapped one nucleotide upstream from that described by Sekar et al.

These results show that the major transcript has as its 5' end the T located at position 1413 (FIG. 3). However, the T located at position 1413 (FIG. 3) might constitute the end of a stable messenger whose true initiation site is located upstream.

Detection and Quantitative Analysis of the Specific mRNA of the cryIIIA Toxin in the Presence of the $H_2$–$H_3$ Fragment The reverse transcriptase is satisfactory for extension from the primers in the case of fragments containing only 100 to 150 bases in as much as this enzyme may stop or be interrupted in regions containing considerable secondary structures at the level of the RNA matrix. In order to study the presence of a potential initiation site for transcription located very far upstream from the 5' end of the cryIIIA gene, a Northern blot analysis was perfumed. The total RNA of the strain bearing pHT305P was recovered at $t_0$, $t_3$, $t_6$ and $t_9$. The RNAs were separated by electrophoresis on agarose gels and hybridized with a probe corresponding to the labelled internal fragments of cryIIIA (PstI-EcoRI fragment d 874 bp). In all of the samples a principal transcript of about 2.5 kb was detected. This is consistent with the size of the transcript defined by the initiation site for transcription described above and a potential termination sequence located about 400 bp downstream from the stop codon of cryIIIA, described by Donovan et al.

The relative quantities of specific mRNA of the CryIIIA twin synthesized by the strain bearing pHT305P and by the strain bearing pHT305H were compared by a dot blot procedure RNAs isolated from synchronous cultures recovered at $t_3$ were immobilized on a nitrocellulose membrane and hybridized with an excess of PstI-EcoRI probe of cryIIIA. The strain bearing pHT305P contained about 10 to 15 times more mRNA specific for cryIIIA than the strain containing pHT305H.

Production of Beta-galactosidase from the Fusion of $H_2$–$H_3$:: lacZ

The relative synthesis of the cryIIIA transcript in the presence and in the absence of the $H_2$–$H_3$ fragment indicated that this DNA segment regulates the expression of the cryIIIA gene at the level of the transcription rather than at the level of translation. Fusion with the lacZ gene was carried out to test the effect produced on transcription by the $H_2$–$H_3$ fragment. The lacZ gene lacking the promoter was subcloned into the SmaI site of pHT304. The resulting plasmid pHT304'lacZ constitutes a system making it possible to generate fusion transcripts and to study their expression in *B. thuringiensis* under conditions approaching those taking place naturally with the cry genes (low copy number plasmid). Consequently, the 713 b $H_3$–$P_1$ fragment was cloned between the HindIII and PstI sites of pHT304'lacZ to give pHT7901'lacZ Finally, the $H_2$–$H_3$ fragment was cloned into the HindIII site of pHT7901'lacZ to give pHT7902'lacZ which bears the $H_2$–$H_3$ fragment in its original orientation with respect to the $H_3$–$P_1$ fragment (FIG. 4). The plasmids pHT7901'lacZ, pHT7902'lacZ and pHT7902'lacZ were introduced into *B. thuringiensis* subspecies Kurstaki HD1 $Cry^-B$ by electroporation. The vector pHT304'lacZ had a blue phenotype potentially attributable to the lacZ promoter or to another DNA region of pUC19 acting as promoter, located upstream from the cloning sites. The sporulation d each strain was induced and samples were taken at $t_{-2}$ and $t_{-1}$ (2 hours and 1 hour before the triggering of sporulation, respectively) and at $t_0$ to $t_{7.5}$ at intervals of 1.5 hour and tested for beta-galactosidase activity (FIG. 5). The beta-galactosidase activity of the strain bearing pHT304'lacZ was constant at about 800 Miller units from $t_{-2}$ to $t_{7.5}$. The level of the production of enzymes of the strain bearing pHT7901'lacZ rose from about 250 Miller units at $t_{-2}$ to about 1,200 Miller units at $t_{7.5}$, indicating a small but significant increase of the beta-galactosidase activity during sporulation (this increase is not apparent because of the scale used in FIG. 5). On the other hand, the recombinant strain bearing pHT7902'lacZ produced much beta-galactosidase (33,000 Miller units at $t_6$ and $t_{7.5}$). Its beta-galactosidase activity increases from about 20 fold between $t_0$ and $t_6$ (FIG. 5). The ratio of the activities of the strains bearing pHT7901'lacZ and pHT7902'lacZ increased from 8 fold during the phase of vegetative growth to about 25 fold during the late phase of sporulation.

The results presented above and more precisely the FIGS. 4 and 5 indicate that the cryIIIA expression system is functional (at low copy number).if the $H_2$–$H_3$ region is present upstream from the $H_3$–$H_1$ region. If this is the case, very high levels of expression are obtained whether with the cryIIIA gene or with the lacZ gene.

1) Precise Definition of the Enhancer Region

Deletions from the $H_2$–$P_1$ fragment (FIG. 3A) showed that a TaqI-TaqI fragment (positions 907 to 1559, FIG. 3) was sufficient to obtain the strong expression of the lacZ gene (plasmid pHT7930'lacZ, FIG. 6).

Furthermore, an internal deletion from the fragment between the PacI and XmnI sites (positions 990 to 1179) does not reduce the expression of the lacZ gene.

This internal deletion led to the introduction of a linker between the PacI and XmnI sites.

The following two nucleotides were synthesized and hybridized together to construct a double-stranded DNA sequence capable of serving as linker between the PacI and XmnI sites (SEQ ID NO:15):

-5'-TAAAGATATCTTTGAAGCTTCACGTGTTTAA ACAGGCCTGCAG-3'—

-3'-TAATTTCTATAGAAACTTCGAAGTGCACAAATT TGTCCGGACGTC-5'—

The linker used here has a sequence such that five nucleotides, naturally present after the PacI site are reconstituted in the plasmid pHT7931'lacZ.

In the presence at this deletion, a better expression seems to be obtained by bringing closer together the two regions TaqI-PacI (positions 907 to 990) and XmnI-TaqI (positions 1179 to 1559) (plasmid pHT7931'lacZ, FIG. 6).

It follows that the cryIIIA expression system requires the association of two distinct DNA sequences; one is included between the TaqI and PacI sites (positions 907 to 990), the other is included between the XmnI and TaqI sites (positions 1179 to 1559).

This conclusion is reinforced by the fact that in the absence of the XmnI-TaqI region (positions 1179 to 1559), the region situated upstream from the XmnI site is not sufficient to obtain the high level of expression of the lacZ gene (plasmid pHT7907'lacZ, FIG. 6). In fact, the DraI-XmnI DNA sequence (positions 806 to 1179) placed upstream from the lacZ gene (plasmid pHT7907'lacZ) makes it possible to obtain in Bt (*B. thuringiensis*) a beta-galactosidase activity of only about 3500 Miller units (to be compared with 30,000 Mu obtained with the plasmid pHT7902'lacZ and pHT17903'lacZ).

Hence this result confirms that the association of the two sequences TaqI-PacI (positions 907 to 990) and XmnI-TaqI (positions 1179 to 1559) is necessary in order for the cryIIIA expression system to be fully functional.

The experiment performed with the DraI-XmnI fragment upstream from lacZ (plasmid pHT7907'lacZ) indicates that a promoter activity is included between DraI and XmnI, and even between TaqI and PacI (positions 907 to 990) since the high beta-galactosidase activity is obtained when the PacI-XmnI fragment (positions 991 to 1179) is absent.

The analysis of the RNAs by primer extension carried out by using an oligonucleotide complementary to the sequence included between the positions 1090 and 1121 in fact makes it possible to detect an initiation of transcription in this region. The latter is located in position 983 (FIG. 3) or more probably at position 984. It follows from this that a promoter must be situated several base pairs upstream from this start. Although there is no obvious homology with known promoters, the −35 (TTGCAA) and −10 (TAAGCT) boxes of the promoter would be expected to be found between the positions 945 to 980.

A MunI-PstI DNA fragment (positions 952 to 1612) placed in front of lacZ (plasmid pHT7909'lacZ) confers a weak beta-galactosidase activity comparable to that obtained with the plasmid pHT7901'lacZ (FIGS. 4 and 5).

This result suggests that the promoter situated at positions 945 and 980 may be inactivated in a contraction starting at MunI (position 952). However, it is known that the minimal sequence necessary for the expression has been defined as starting at the TaqI site (position 907).

It follows from these different experiments that a DNA sequence located between the TaqI and PacI sites (positions 907 to 990) is required in order to obtain a high expression of lacZ and, consequently, a high level of transcription of cryIIIA.

Measurement of the Activity of the Upstream Promoter in the cryIIIA Expression System In order to measure the activity of the upstream promoter, a transcriptional fusion was constructed with the DNA fragment containing this promoter and the lacZ gene. For this the expression vector pHT304-18Z was first constructed (FIG. 8A). The DNA fragment included between the positions 907 and 990 was then cloned upstream of the lacZ gene to give the plasmid pHT7832'lacZ The beta-galactosidase activity is 3,000 U/ml of proteins at $t_0$ and 13,000 U/mg of proteins at $t_6$ (FIG. 8B).

The role of the upstream promoter in the global activity of the cryIIIA expression system was evaluated by analyzing the effect produced by its inactivation. The MunI restriction site was filled in with the aid of the Klenow fragment of the DNA polymerase in the presence of deoxynucleotides to give the plasmid pHT7832ΔMunI'lacZ. This leads to the addition of 4 nucleotides between the -35 and -10 regions of the promoter (CAATTAATTG SEQ ID NO:17 versus CAATTG). The beta-galactosidase activity of the strain bearing pHT7832ΔMunI'lacZ was about 10 U/mg of proteins at $t_0$ and about 30 U/mg of proteins at $t_6$ age (FIG. 8B). This result indicates that the upstream promoter is then inactivated. The DNA fragment containing the modified MunI site was introduced into the plasmid pHT7830'lacZ to give the plasmid pHT7830ΔMunI'lacZ. The beta-galactosidase activity of the strain bearing pHT7830ΔMunI'lacZ was about 25 U/mg of proteins at to and about 450 U/mg of proteins at $t_6$ (FIG. 8B). By comparison with the strain bearing the plasmid pHT7830'lacZ, it follows that the upstream promoter is necessary for the optimal functioning of the cryIIIA expression system. The plasmid pHT7830'lacZ corresponds to the vector pHT304-18Z in which is doned the TaqI fragment containing the entire cryIIIA expression system.

Study of the Role of the Downstream Region in the cryIIIA Expression System

The preceding results confirm that the upstream promoter is necessary for the optimal functioning of the cryIIIA expression system; an the other hand, it is not sufficient to account for the maximal activity of the entire system. This latter aspect had been mentioned previously (compare the beta-galactosidase activity of the strains bearing the plasmids pHT7832'lacZ and pHT7831'lacZ (FIG. 8B). The plasmid pHT7831'lacZ corresponds to the plasmid pHT7830'lacZ, the internal fragment PacI-XmnI of which is deleted. It follows that a region called "downstream" is required to explain the maximal activity of the cryIIIA expression system.

The transcription initiation site of the cryIIIA gene had been previously localized in position 1413, the −35 and −10 regions of the putative promoter ought to be included between the nucleotides 1370 and 1412 (Sekar et al., 1987, Proc. Natl. Acad. Sci. USA, 84: 7036–7040). In order to assess the efficacy of this putative promoter, we have constructed the plasmid pHT7815/8'lacZ in which the DNA fragment included between the nucleotides 1352 and 1412 was deleted. The beta-galactosidase activity of the strain bearing pHT7815/8'lacZ was about 3,000 U/mg of proteins at to and about 42,000 U/mg of proteins at $t_6$ (FIG. 8B. This result indicates that the region included between the nucleotides 1362 and 1412 does not play an essential role in the cryIIIA expression system and can not therefore be considered as the promoter of the cryIIIA gene.

A primer extension experiment was carried out with the total RNAs extracted at $t_3$ from a *B. thuringiensis* strain bearing the plasmid pHT7815/8'lacZ. The 5' end of the major transcript is detected as previously at position 1413 (FIG. 9). All of our results thus demonstrate that this end does not correspond to transcription initiation but to the end of a stable transcript initiated at position 984 starting from a upstream promoter localized in the DNA region included between the TaqI and PacI sites (positions 907 to 990) and defined by the −35 and −10 regions: TTGCAA and TAAGCT. Since the 5' end of the major cryIIIA transcript is invariably in position 1413, in the presence or in the absence of the DNA fragment included between the positions 1362 and 1412, it follows that this end is defined by the presence of a DNA sequence which is found downstream of the position 1413. The role of this region is thus exerted at the post-transcriptional level. The analysis of this downstream sequence was made in *B. subtilis* with the aid of transcriptional fusions with the lacZ gene. The various constructions presented in FIG. 10 have enabled us to define more precisely the downstream region and to measure its post-transcriptional effect:

1. The DNA fragment included between the nucleotides 1462 and 1556 was deleted from the plasmid pHT7830'lacZ to give the plasmid pHT7816'lacZ. The beta-galactosidase activity of the strain bearing pHT7816'lacZ was about 25,000 U/mg of proteins at $t_3$ whereas the beta-galactosidase activity of the strain bearing pHT7830'lacZ was about 50,000 U/mg of proteins at $t_3$ (FIG. 10).
2. The DNA fragment included between the nucleotide 1413 and 1556 was deleted from the plasmid pHT7830'lacZ to give the plasmid pHT7805'lacZ. The beta-galactosidase activity of the strain bearing pHT7805'lacZ was about 5,000 U/mg of proteins at $t_3$ (FIG. 10).
3. The nucleotides GGA in position 1421–1423 of the plasmid pHT7830'lacZ were replaced by the nucleotide CCC to give the plasmid pHT7830Rm'lacZ. The beta-galactosidase activity of the strain bearing pHT7830Rm'lacZ was about 5,000 U/mg of proteins at $t_3$ (FIG. 10).
4. A primer extension experiment was carried out with the total RNAs extracted at $t_3$ from a *B. thuringiensis* strain bearing the plasmid pHT7830Rm'lacZ. The 5' end d the major transcript is detected at position 984 and no transcript having a 5' end at position 1413 is detected.

These four results indicate that the post-transcriptional effect of the downstream region is principally due to the nucleotide sequence included between the nucleotides 1413 and 1461. Furthermore, the nucleotides GGA in position 1421–1423 are important far conferring the post-transcriptional effect and might be modified only by considering replacement by a sequence ensuring an intensity of interaction with the 16S ribosomal RNA similar to the intensity of interaction measured for the nucleotides GGA For example, the replacement of the nucleotides GGA by the nucleotides CCC leads to the complete disappearance of the post-transcriptional effect, explained by a considerable modification of the intensity of interaction between this portion of the segment and the 16S RNA The downstream region thus defined has as distinctive characteristic that of containing a nucleotide sequence complementary to the 3' end of the 16S RNA of ribosomes.

The post-transcriptional effect of this DNA sequence has then been evaluated by using a heterologous expression system: the following DNA sequence (S1) (nucleotides 1–38 of SEQ ID NO:9).

5'-AGCTTGAAAGGAGGGATGCCTAAAAACGAAGA ACTGCA-3'

3'-ACTTTCCTCCCTACGGATTTTTGCTTCTTG-5' was synthesized and cloned between the HindIII and PstI sites of the vector pHT304'lacZ to give the plasmid pHT304ΩRS1'lacZ. This DNA sequence is thus intercalated between the promoter of the lacZ gene and the sequence coding for the lacZ gene.

The beta-galactosidase activity of the strain 168 of *B. subtilis* bearing pHT304ΩRS1'lacZ was about 4,000 U/mg of proteins at $t_3$. It follows that the sequence described above increases by a factor of 4 the expression of the lacZ gene. This increase is comparable to the increase due to the region included between the nucleotides 1413 and 1461, i.e. by a factor of 5 (compare the beta-galactosidase activity of the B. subtilis strains containing the plasmids pHT7816'lacZ or pHT7805'lacZ). The following DNA region is thus sufficient to confer the post-transcriptional effect to the cryIIIA expression system (nucleotides 1–32 of SEQ ID NO:10):

5'-CTTGAAAGGAGGGATGCCTAAAAACGAAG AAC-3'

3'-GAACTTTCCTCCCTACGGATTTTTGCTTCTTG-5'

This sequence possesses a region complementary to the 3' end of the 16S ribosomal RNA. However, other elements characteristic of the downstream region of the cryIIIA expression system and which may accentuate this effect, in particular by preventing the movement of the ribosome, are probably comprised in the nucleotide sequence included between positions 1462 and 1556. Their presence seems to explain the difference of beta-galactosidase activity observed between the *B. subtilis* strain containing the plasmid pHT7830'lacZ (50,000 U/mg of proteins at $t_3$) and the *B. subtilis* strain containing the plasmid pHT7816'lacZ (25,000 U/mg of proteins at $t_3$; see FIG. 10).

These results thus seem to confirm that the post-transcriptional effect of the downstream region results from the hybridization between the 16S ribosomal RNA and the S2 sequence of the messenger RNA of cryIIIA. It is hence probable that the ribosome or a part of the ribosome binds to this downstream region of the RNA and thus protects it from exonucleolytic degradation initiated at 5'. As previously mentioned, this binding would thus have the effect of enhancing the stability of the messengers and thus of increasing the level of expression of a given gene. That explains why the 5' end of the cryIIIA transcripts is invariably at position 1413 irrespective of where transcription is initiated. This mechanism also seems to be confirmed by the positive effect of the S1 sequence on a heterologous expression system (plasmid pHT304'IIRS1lacZ in the strain 168 of *B. subtilis*).

Introduction of the Fusion {CryIIIA—LacZ Expression System} into the Chromosome of *Bacillus subtilis.*

The vector pAF1, non-replicative in *B. subtilis* enables the fusions with the LacZ reporter gene to be introduced into the *B. subtilis* chromosome at the amyE locus (J. Bact. 1990, 172: 835–844). The plasmid pHC1 is obtained by insertion at the HindIII-SacI fragment (2.7 kb) of the pHT7901'LacZ between the HindIII-SacI sites of pAF1.

The plasmid pHC2 is obtained by insertion of the HindIII-SacI fragment (3.7 kb) of the pHT7902'LacZ between the HindIII and SacI sites of pAF1.

The fusions are introduced into the *B. subtilis* strain 168 trpC2 (Anagnostopoulos, C and Spizizen, J. 1961 J. Bacteriol. 81: 741–746) (Bacillus subtilis 168) by transformation; the {amy-} phenotype accounts for the integration by double recombination.

Study of the Expression System of the cryIIIA gene in *B. subtilis.*

The *B. subtilis* strains obtained after transformation and integration of the pHC1 and pHC2 plasmids are called respectively:

Bs168 {H} and Bs168 {P}

The construction contained in the plasmid pHC2, i.e. bearing the $H_2$–$P_1$ fragment upstream from the lacZ, was also introduced into the *B. subtilis* strain Δ sigE.

The strain Δ sigE is obtained by transforming a parental strain ($Spo^+$) with a plasmid non-replicative in Gram-positive bacteria and bearing a sigE gene, the internal region of which is deleted. The sigE gene was described by Stragier et al 1984 Nature 312: 376–378.

The strain Δ sigE is transformed with the plasmid pHC2 and the resulting strain is Δ sigE {P}.

The gene coding for the sigmaE factor specific for sporulation has been deleted from this strain. This strain is hence asporogenic ($Spo^-$).

Similarly, the strain Bs 168 {P} was transformed with a "$Km^R$ cassette" which interrupts the SpoOA gene. The strain in which the SpoOA gene interrupted by a "KmR cassette" originates is obtained by transforming a parental strain ($Spo^+$) with a plasmid, non-replicative in Gram-positive bacteria and bearing a SpoOA gene (described by Ferrari, F. A. et al. 1985 PNAS USA 82: 2647–2651) interrupted by a gene for resistance to kanamycin. The chromosomal DNA of this strain was used to transform the strain Bs 168 {P}.

Thus, the resulting Spo-strain was called Bs 168 SpoOA {P}.

Firstly, it appears that the production of beta-galactosidase obtained with the strain of *B. subtilis* 168 {H} is very low (<100 μM) by comparison with the strain 168 {P} (about 15,000 μM). These results are similar to those obtained in Bt.

Furthermore, a very surprising result was obtained: the expression in the strain BsΔsigE is identical with the expression in the wild type strain Bs 168. This result indicates that the cryIIIA gene is not controlled by a specific promoter at the sigma E factor as is the case for the cryIA gene.

It is even more surprising that the expression in the strain Bs SpoOA {P} is higher than that obtained in the strain Bs 168 {P}. This result shows that the expression of is independent of sporulation since the SpoOA gene is implicated in the first stage of sporulation.

These results are very important for the development and the applications of the cryIIIA expression system. They in fact indicate that it is possible to envisage the production of the insecticidal toxins or of any other protein of commercial interest in $Spo^-$ strains of *B. subtilis* or *B. thuringiensis.*

Analysis of the Expression of the Fusion {CryIIIA-LacZ Expression System=pHC2} in *Bacillus subtilis* as a Function of the Culture Medium.

It is possible to make the flowing observations as regards the expression of the fusion in the media 1 to 5, respectively, the composition of which is given below, Expression (although weak) occurs during the vegetative phase.

Expression increases at the beginning of the stationary phase.

The comparison of media 2 (deficient in phosphate) and 5 (deficient in amino acids) show that the CryIIIA expression system is activated by the amino acids deficiency.

The expression in medium 4 shows that this activation requires the presence of salts: $CaCl_2$, $MnCl_2$, AFC.

The activation is independent of sporulation:

In sporulation medium 1 (Sp medium) expression stops at $t_2$.

In the medium 5 the cells cannot sporulate (glucose inhibits sporulation) and activation is maximum.

When the only nitrogen source is $NH^+_4$, the activation is lower, expression, however, remains considerable (medium 3).

1/Sp Medium: Sporulation Medium 8 g nutrient broth (Difco)/liter 1 mM $MgSO_4$

13mM KCl

10 μM $MnCl_2$

1 μM $FeSO_4$

1 μM $CaCl_2$

2/Phosphate Deficient Medium

HEPES buffer pH 7; 50 mM 1 mM $MgSO_4$ 0.5 mM $CaCl_2$

10 M $MnCl_2$ 4.4 mg/liter ammonium ferric citrate (AFC)

2% glucose 10 mM KCl 100 mg/liter of each amino acid 50 mg/liter tryptophan 0.45 mM phosphate buffer, pH 7

3/Minimal Medium 44 mM $KH_2PO_4$ 60 mM $K_2HPO_4$ 2.9 mM Trisodium citrate 15 mM $(NH_4)_2SO_4$ 2% glucose 4/Amino Acid Deficient Medium Without $CaCl_2$, $MnCl_2$, AFC 44 mM $KH_2PO_4$ 60 mM $K_2HPO_4$ 2.9 mM Trisodium citrate 2% glucose 1 mM $MgSO_4$ 50 mg/liter tryptophan 0.5 casein hydrolysate (CH)

5/4 idem by Adding;

0.5 mM $CaCl_2$

10 M $MnCl_2$ 4.4 mg/liter AFC

Construction of a *B. thuringiensis* $Sp^-$ strain

Cloning of the spoOA gene of *B. thuringiensis:*

The total DNA of the *B. thuringiensis* strain 407 of serotype 1 was purified and digested by the enzyme HindIII. The HindIII fragments were ligated with the vector pHT304 digested by HindIII and the ligation mixture was used to transform the *B. subtilis* strain 168. The transformant clones were selected for resistance to erythromycin. They were then transformed with the total DNA of the *B. subtilis* strain 168, the spoOA gene of which was interrupted by a "$Km^R$ cassette". The transformant clones which had become resistant to kanamycin and which still had a $Spo^+$ phenotype were studied. One of the clones carried a recombinant plasmid capable of compensating the spoOA mutation of *B. subtilis*. This plasmid was constituted by the vector pHT304 and a HindIII fragment of about 24 kb (FIG. 11A).

Determination of the Nucleotide Sequence of the spoOA Gene of *B. thuringiensis:*

The nucleotide sequence of the HindIII fragment was determined and revealed the presence of an open reading frame of 804 bp capable of coding for a protein of 264 amino acids homologous to the SpoOA protein of *B. subtilis*. The nucleotide sequence of 804 bp of the spoOA gene of *B. thuringiensis* strain 407 is shown in FIG. 11B.

Interruption of the spoOA Gene of *B. thuringiensis:*

A 1.5 kb DNA fragment being an aphIII gene, conferring resistance to kanamycin ("cassette $Km^R$"), was inserted between the two HincII sites of the spoOA gene (FIG. 11) A 40 bp fragment included between the positions 267 and 307 of the spoOA gene was thus replaced by the "$Km^R$ cassette". The HindIII DNA fragment of about 3.9 kb containing the spoOA gene interrupted by the "$Km^R$ cassette" was cloned in the thermosensitive vector pRN5101 (Villafane et al. 1987, J. Bacteriol. 169: 4822–4829). The resulting plasmid (designated pHT5120) was introduced in the *B. thuringiensis* strain 407 $Cry^-$ by electroporation. The spoOA gene of the *B. thuringiensis* strain 407 $Cry^-$ was replaced by the copy interrupted with the "$Km^R$ cassette" by genetic recombination in vivo by using the protocol previously described (Lereclus et al., 1992, Bio/Technology 10: 418–421). The resultant *B. thuringiensis* strain (designated 407-OA:: KmR) is resistant to kanamycin (300 $\mu$g/ml) and does not produce spares when it is cultured in HCT medium, usually favorable to the sporulation of *B. thuringiensis*. A DNA/DNA hybridization easement perfumed with the 2.4 kb HindIII fragment as probe revealed that the spoOA gene of the *B. thuringiensis* strain 407 $Cry^-$ has indeed been replaced by the copy interrupted with the "$Km^R$ cassette".

Production of the CryIIIA Toxin in the *B. thuringiensis* Strain 407-OA:: $Km^R$:

The plasmid pHT305P bearing the cryIIIA gene was introduced into the *B. thuringiensis* strain 407-OA:: KmR by electroporation. The recombinant clone obtained was deposited with the CNCM on Mar. 5, 1994 and to which the access number I-1412 was assigned. The recombinant clone obtained was cultured at 30° C. in HCT medium+glucose 3 g/l or in LB medium (NaCl, 5 g/l; yeast extract, 5 g/l; Bacto tryptone 10 g/l) to estimate the production of toxins. After about 48 hours the bacteria contained a crystal visible by examination with the optical microscope. This crystal was rhomboidal, characteristic of the crystals constituted by the CryIIIA protein. The crystals produced by the *B. thuringiensis* strain 407-OA:: KmR {pHT315} are of considerable size and remain included in the cells several days after the latter have ceased to develop in HCT medium; in LB medium a portion of the cells lyse and the crystals are released. The crystals are constituted of proteins of about 70 kDa (CryIIIA) specifically toxic for the Coleoptera.

What is claimed is:

1. DNA isolated sequence comprising (a) a promoter sequence from the fragment comprising nucleotides 907 to 990 of SEQ ID NO:1, (b) a region from a DNA sequence comprising nucleotides 979 to 1692, defined by the restriction sites HindIII-Pstl (H3-P1) of SEQ ID NO:1, which enhances the expression in a host cell of a coding sequence placed downstream.

2. An isolated DNA sequence comprising SEQ ID NO:1, SEQ ID NO:2, or SEQ ID NO:3.

3. The isolated DNA sequence of claim 2, which promotes the expression of a nucleotide sequence placed downstream.

4. A recombinant DNA, comprising the isolated DNA sequence of claim 2 and a nucleotide coding sequence downstream of the isolated DNA sequence.

5. An expression vector comprising the isolated DNA sequence of claim 2.

6. A recombinant cell host comprising the isolated DNA sequence of claim 2.

7. The isolated DNA sequence of claim 2, which comprises SEQ ID NO:1.

8. A recombinant DNA, comprising the isolated DNA sequence of claim 7 and a nucleotide coding sequence downstream of the isolated DNA sequence.

9. An expression vector comprising the isolated DNA sequence of claim 7.

10. A recombinant cell host comprising the isolated DNA sequence of claim 7.

11. The isolated DNA sequence of claim 2, which comprises SEQ ID NO:2.

12. A recombinant DNA, comprising the isolated DNA sequence of claim 11 and a nucleotide coding sequence downstream of the isolated DNA sequence.

13. An expression vector comprising the isolated DNA sequence of claim 11.

14. A recombinant cell host comprising the isolated DNA sequence of claim 11.

15. The isolated DNA sequence of claim 2, which comprises SEQ ID NO:3.

16. A recombinant DNA, comprising the isolated DNA sequence of claim 15 and a nucleotide coding sequence downstream of the isolated DNA sequence.

17. An expression vector comprising the isolated DNA sequence of claim 15.

18. A recombinant cell host comprising the isolated DNA sequence of claim 15.

19. An isolated DNA sequence, which hybridizes under stringent conditions to the isolated DNA sequences of claim 2.

20. The isolated DNA sequence of claim 19, which promotes the expression of a nucleotide sequence placed downstream.

21. A recombinant DNA, comprising the isolated DNA sequence of claim 19 and a nucleotide coding sequence downstream of the isolated DNA sequence.

22. An expression vector comprising the isolated DNA sequence of claim 19.

23. A recombinant cell host comprising the isolated DNA sequence of claim 19.

24. An isolated DNA, which consists essentially of SEQ ID NO:4, SEQ ID NO:5, SEQ ID NO:8, SEQ ID NO:10, or SEQ ID NO:11.

25. The isolated DNA of claim 24, which consists essentially of SEQ ID NO:4.

26. A recombinant DNA, comprising the isolated DNA sequence of claim 25 and a nucleotide coding sequence downstream of the isolated DNA sequence.

27. An expression vector comprising the isolated DNA sequence of claim 25.

28. A recombinant cell host comprising the isolated DNA sequence of claim 25.

29. The isolated DNA of claim 24, which consists essentially of SEQ ID NO:5.

30. A recombinant DNA, comprising the isolated DNA sequence of claim 29 and a nucleotide coding sequence downstream of the isolated DNA sequence.

31. An expression vector comprising the isolated DNA sequence of claim 29.

32. A recombinant cell host comprising the isolated DNA sequence of claim 29.

33. The isolated DNA of claim 24, which consists essentially of SEQ ID NO:8.

34. A recombinant DNA, comprising the isolated DNA sequence of claim 33 and a nucleotide coding sequence downstream of the isolated DNA sequence.

35. An expression vector comprising the isolated DNA sequence of claim 33.

36. A recombinant cell host comprising the isolated DNA sequence of claim 33.

37. The isolated DNA of claim 24, Which consists essentially of SEQ ID NO:10.

38. A recombinant DNA, comprising the isolated DNA sequence of claim 37 and a nucleotide coding sequence downstream of the isolated DNA sequence.

39. An expression vector comprising the isolated DNA sequence of claim 37.

40. A recombinant cell host comprising the isolated DNA sequence of claim 37.

41. The isolated DNA of claim 24, which consists essentially of SEQ ID NO:11.

42. A recombinant DNA, comprising the isolated DNA sequence of claim 41 and a nucleotide coding sequence downstream of the isolated DNA sequence.

43. An expression vector comprising the isolated DNA sequence of claim 41.

44. A recombinant cell host comprising the isolated DNA sequence of claim 41.

* * * * *

UNITED STATES PATENT AND TRADEMARK OFFICE

CERTIFICATE OF CORRECTION

PATENT NO. : 6,555,366 B1
DATED : April 29, 2003
INVENTOR(S) : Lereclus et al.

It is certified that error appears in the above-identified patent and that said Letters Patent is hereby corrected as shown below:

Title page,
Item [63], should read:

-- Related U.S. Application Data

[63] Continuation of application No. 08/535,057, filed as application No PCT/FR94/00525, on May 5, 1994, now Pat. No. 6,140,104. --

Signed and Sealed this

Twenty-third Day of December, 2003

JAMES E. ROGAN
*Director of the United States Patent and Trademark Office*

```
SEQUENCE LISTING

(1) GENERAL INFORMATION:

   (iii) NUMBER OF SEQUENCES: 17

(2) INFORMATION FOR SEQ ID NO: 1:

     (i) SEQUENCE CHARACTERISTICS:
          (A) LENGTH: 1692 base pairs
          (B) TYPE: nucleic acid
          (C) STRANDEDNESS: single
          (D) TOPOLOGY: linear

    (ii) MOLECULE TYPE: DNA (genomic)

    (xi) SEQUENCE DESCRIPTION: SEQ ID NO: 1:
```

-continued

```
AAGCTTTCAG TGAAGTACGT GATTATACGG AGATGAAAAT TCGTACACTG TTAACGAGAA     60

GGAAACGCCG ACGAAAGCGT AGCATCGGAT GGCAAAGATG GAGTAACGAA TATCTCTACG    120

GTGTACTGGG GCTTTACTGA GACTAGAAAG TCCTTCCCTT GAAAAGTGCA GAGAGTTTTC    180

GATAAAAGTG TCAGCCATTT GATAAGTCTC ATTCTCATAA CCTATTGATG AAGTTTATAG    240

GGAAGCTGCT TGAGAGGGAA AACCTCACGA ACAGTTCTTA TGGGGAGAGA CTGGAAACAG    300

GTCACAATTG ATACCTCGCT AATCTTTTAA CCGACAAAGT TTTTTTAAAC CGTGGAAGTC    360

ATAATAACCT GGATATTGTG AATTTATAAA AGTTAACAAA TGGTTTATAT TAAGACAGTC    420

ATAAACCAAA GATTTTTCTT CTAAAGCTAC GATAGCAAAA ATTTCACTAG AAATTAGTTA    480

TACAAGCATT TTGTAAGAAT TATTAAAAAG ATAAATCCTG CTATTACGAG ATTAGTAGGA    540

TGATATTGTG AAAAATTTTT TATCTATTCG ATTTAAAATA TTTATGAATT TTACATAAAC    600

CTCATAAGAA AAAATACTAT CTATACTATT TTAAGAAATT TATTAGAATA AGCGGATTCA    660

AAATAGCCCT GGCCATAAAA GTACCTCAGC AGTAGAAGTT TTGACCAAAA TTAAAAAAAT    720

ACCCAATCAA GAGAATATTC TTAATTACAA TACGTTTTGC GAGGAACATA TTGATTGAAA    780

TTTAATAAAT TTAGTCCTAA AATTTAAAGA AATTTAAGTT TTTCATATTT TTATGAACTA    840

ACAAGAATAA AAATTGTGTT TATTTATTAT TCTTGTTAAA TATTTGATAA AGAGATATAT    900

TTTTGGTCGA AACGTAAGAT GAAACCTTAG ATAAAAGTGC TTTTTTTGTT GCAATTGAAG    960

AATTATTAAT GTTAAGCTTA ATTAAAGATA ATATCTTTGA ATTGTAACGC CCCTCAAAAG   1020

TAAGAACTAC AAAAAAAGAA TACGTTATAT AGAAATATGT TTGAACCTTC TTCAGATTAC   1080

AAATATATTC GGACGGACTC TACCTCAAAT GCTTATCTAA CTATAGAATG ACATACAAGC   1140

ACAACCTTGA AAATTTGAAA ATATAACTAC CAATGAACTT GTTCATGTGA ATTATCGCTG   1200

TATTTAATTT TCTCAATTCA ATATATAATA TGCCAATACA TTGTTACAAG TAGAAATTAA   1260

GACACCCTTG ATAGCCTTAC TATACCTAAC ATGATGTAGT ATTAAATGAA TATGTAAATA   1320

TATTTATGAT AAGAAGCGAC TTATTTATAA TCATTACATA TTTTTCTATT GGAATGATTA   1380

AGATTCCAAT AGAATAGTGT ATAAATTATT TATCTTGAAA GGAGGGATGC CTAAAAACGA   1440

AGAACATTAA AAACATATAT TTGCACCGTC TAATGGATTT ATGAAAAATC ATTTTATCAG   1500

TTTGAAAATT ATGTATTATG ATAAGAAAGG GAGGAAGAAA AATGAATCCG AACAATCGAA   1560

GTGAACATGA TACAATAAAA ACTACTGAAA ATAATGAGGT GCCAACTAAC CATGTTCAAT   1620

ATCCTTTAGC GGAAACTCCA AATCCAACAC TAGAAGATTT AAATTATAAA GAGTTTTTAA   1680

GAATGACTGC AG                                                        1692
```

(2) INFORMATION FOR SEQ ID NO: 2:

(i) SEQUENCE CHARACTERISTICS:
(A) LENGTH: 653 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: misc_feature
(B) LOCATION: 1..653
(D) OTHER INFORMATION: /note= "NUCLEOTIDES 907 TO 1559 OF SEQ ID NO:1"

(xi) SEQUENCE DESCRIPTION: SEQ ID NO: 2:

```
TCGAAACGTA AGATGAAACC TTAGATAAAA GTGCTTTTTT TGTTGCAATT GAAGAATTAT     60
```

-continued

```
TAATGTTAAG CTTAATTAAA GATAATATCT TTGAATTGTA ACGCCCCTCA AAAGTAAGAA    120

CTACAAAAAA AGAATACGTT ATATAGAAAT ATGTTTGAAC CTTCTTCAGA TTACAAATAT    180

ATTCGGACGG ACTCTACCTC AAATGCTTAT CTAACTATAG AATGACATAC AAGCACAACC    240

TTGAAAATTT GAAAATATAA CTACCAATGA ACTTGTTCAT GTGAATTATC GCTGTATTTA    300

ATTTTCTCAA TTCAATATAT AATATGCCAA TACATTGTTA CAAGTAGAAA TTAAGACACC    360

CTTGATAGCC TTACTATACC TAACATGATG TAGTATTAAA TGAATATGTA AATATATTTA    420

TGATAAGAAG CGACTTATTT ATAATCATTA CATATTTTTC TATTGGAATG ATTAAGATTC    480

CAATAGAATA GTGTATAAAT TATTTATCTT GAAAGGAGGG ATGCCTAAAA ACGAAGAACA    540

TTAAAAACAT ATATTTGCAC CGTCTAATGG ATTTATGAAA AATCATTTTA TCAGTTTGAA    600

AATTATGTAT TATGATAAGA AAGGGAGGAA GAAAAATGAA TCCGAACAAT CGA           653
```

(2) INFORMATION FOR SEQ ID NO: 3:

(i) SEQUENCE CHARACTERISTICS:
(A) LENGTH: 84 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: misc_feature
(B) LOCATION: 1..84
(D) OTHER INFORMATION: /note= "NUCLEOTIDES 907 TO 990 OF SEQ ID NO:1"

(xi) SEQUENCE DESCRIPTION: SEQ ID NO: 3:

```
TCGAAACGTA AGATGAAACC TTAGATAAAA GTGCTTTTTT TGTTGCAATT GAAGAATTAT     60

TAATGTTAAG CTTAATTAAA GATA                                            84
```

(2) INFORMATION FOR SEQ ID NO: 4:

(i) SEQUENCE CHARACTERISTICS:
(A) LENGTH: 381 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: misc_feature
(B) LOCATION: 1..381
(D) OTHER INFORMATION: /note= "NUCLEOTIDES 1179 TO 1559 OF SEQ ID NO:1"

(xi) SEQUENCE DESCRIPTION: SEQ ID NO: 4:

```
TTGTTCATGT GAATTATCGC TGTATTTAAT TTTCTCAATT CAATATATAA TATGCCAATA     60

CATTGTTACA AGTAGAAATT AAGACACCCT TGATAGCCTT ACTATACCTA ACATGATGTA    120

GTATTAAATG AATATGTAAA TATATTTATG ATAAGAAGCG ACTTATTTAT AATCATTACA    180

TATTTTTCTA TTGGAATGAT TAAGATTCCA ATAGAATAGT GTATAAATTA TTTATCTTGA    240

AAGGAGGGAT GCCTAAAAAC GAAGAACATT AAAAACATAT ATTTGCACCG TCTAATGGAT    300

TTATGAAAAA TCATTTTATC AGTTTGAAAA TTATGTATTA TGATAAGAAA GGGAGGAAGA    360

AAAATGAATC CGAACAATCG A                                              381
```

(2) INFORMATION FOR SEQ ID NO: 5:

-continued (i) SEQUENCE CHARACTERISTICS:
(A) LENGTH: 378 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: misc_feature
(B) LOCATION: 1..378
(D) OTHER INFORMATION: /note= "NUCLEOTIDES 1179 TO 1556 OF SEQ ID NO:1"

(xi) SEQUENCE DESCRIPTION: SEQ ID NO: 5:

```
TTGTTCATGT GAATTATCGC TGTATTTAAT TTTCTCAATT CAATATATAA TATGCCAATA     60

CATTGTTACA AGTAGAAATT AAGACACCCT TGATAGCCTT ACTATACCTA ACATGATGTA    120

GTATTAAATG AATATGTAAA TATATTTATG ATAAGAAGCG ACTTATTTAT AATCATTACA    180

TATTTTTCTA TTGGAATGAT TAAGATTCCA ATAGAATAGT GTATAAATTA TTTATCTTGA    240

AAGGAGGGAT GCCTAAAAAC GAAGAACATT AAAAACATAT ATTTGCACCG TCTAATGGAT    300

TTATGAAAAA TCATTTTATC AGTTTGAAAA TTATGTATTA TGATAAGAAA GGGAGGAAGA    360

AAAATGAATC CGAACAAT                                                  378
```

(2) INFORMATION FOR SEQ ID NO: 6:

(i) SEQUENCE CHARACTERISTICS:
(A) LENGTH: 591 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: misc_feature
(B) LOCATION: 1..447
(D) OTHER INFORMATION: /note= "NUCLEOTIDES 1 TO 447 CORRESPOND TO NUCLEOTIDES 907 TO 1353 OF SEQ ID NO:1"

(ix) FEATURE:
(A) NAME/KEY: misc_feature
(B) LOCATION: 448..591
(D) OTHER INFORMATION: /note= "NUCLEOTIDES 448 TO 591 CORRESPOND TO NUCLEOTIDES 1413 TO 1556 OF SEQ ID NO:1"

(xi) SEQUENCE DESCRIPTION: SEQ ID NO: 6:

```
TCGAAACGTA AGATGAAACC TTAGATAAAA GTGCTTTTTT TGTTGCAATT GAAGAATTAT     60

TAATGTTAAG CTTAATTAAA GATAATATCT TTGAATTGTA ACGCCCCTCA AAAGTAAGAA    120

CTACAAAAAA AGAATACGTT ATATAGAAAT ATGTTTGAAC CTTCTTCAGA TTACAAATAT    180

ATTCGGACGG ACTCTACCTC AAATGCTTAT CTAACTATAG AATGACATAC AAGCACAACC    240

TTGAAAATTT GAAAATATAA CTACCAATGA ACTTGTTCAT GTGAATTATC GCTGTATTTA    300

ATTTTCTCAA TTCAATATAT AATATGCCAA TACATTGTTA CAAGTAGAAA TTAAGACACC    360

CTTGATAGCC TTACTATACC TAACATGATG TAGTATTAAA TGAATATGTA AATATATTTA    420

TGATAAGAAG CGACTTATTT ATAATCATCT TGAAAGGAGG GATGCCTAAA AACGAAGAAC    480

ATTAAAAACA TATATTTGCA CCGTCTAATG GATTTATGAA AAATCATTTT ATCAGTTTGA    540

AAATTATGTA TTATGATAAG AAAGGGAGGA AGAAAAATGA ATCCGAACAA T             591
```

(2) INFORMATION FOR SEQ ID NO: 7:

(i) SEQUENCE CHARACTERISTICS:

-continued (A) LENGTH: 465 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: misc_feature
(B) LOCATION: 1..84
(D) OTHER INFORMATION: /note= "NUCLEOTIDES 1 TO 84 CORRESPOND TO NUCLEOTIDES 907 TO 990 OF SEQ ID NO:1"

(ix) FEATURE:
(A) NAME/KEY: misc_feature
(B) LOCATION: 85..465
(D) OTHER INFORMATION: /note= "NUCLEOTIDES 85 TO 465 CORRESPOND TO NUCLEOTIDES 1179 TO 1559 OF SEQ ID NO:1"

(xi) SEQUENCE DESCRIPTION: SEQ ID NO: 7:

TCGAAACGTA AGATGAAACC TTAGATAAAA GTGCTTTTTT TGTTGCAATT GAAGAATTAT 60

TAATGTTAAG CTTAATTAAA GATATTGTTC ATGTGAATTA TCGCTGTATT TAATTTTCTC 120

AATTCAATAT ATAATATGCC AATACATTGT TACAAGTAGA AATTAAGACA CCCTTGATAG 180

CCTTACTATA CCTAACATGA TGTAGTATTA AATGAATATG TAAATATATT TATGATAAGA 240

AGCGACTTAT TTATAATCAT TACATATTTT TCTATTGGAA TGATTAAGAT TCCAATAGAA 300

TAGTGTATAA ATTATTTATC TTGAAAGGAG GGATGCCTAA AAACGAAGAA CATTAAAAAC 360

ATATATTTGC ACCGTCTAAT GGATTTATGA AAAATCATTT TATCAGTTTG AAAATTATGT 420

ATTATGATAA GAAAGGGAGG AAGAAAAATG AATCCGAACA ATCGA 465

(2) INFORMATION FOR SEQ ID NO: 8:

(i) SEQUENCE CHARACTERISTICS:
(A) LENGTH: 49 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: misc_feature
(B) LOCATION: 1..49
(D) OTHER INFORMATION: /note= "CORRESPONDS WITH NUCLEOTIDES 1413 TO 1461 OF SEQ ID NO:1"

(xi) SEQUENCE DESCRIPTION: SEQ ID NO: 8:

TCTTGAAAGG AGGGATGCCT AAAAACGAAG AACATTAAAA ACATATATT 49

(2) INFORMATION FOR SEQ ID NO: 9:

(i) SEQUENCE CHARACTERISTICS:
(A) LENGTH: 38 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO: 9:

AGCTTGAAAG GAGGGATGCC TAAAAACGAA GAACTGCA 38

(2) INFORMATION FOR SEQ ID NO: 10:

(i) SEQUENCE CHARACTERISTICS:
(A) LENGTH: 32 base pairs
(B) TYPE: nucleic acid

-continued (C) STRANDEDNESS: double
(D) TOPOLOGY: linear (ii) MOLECULE TYPE: DNA (genomic)

(xi) SEQUENCE DESCRIPTION: SEQ ID NO: 10:

CTTGAAAGGA GGGATGCCTA AAAACGAAGA AC 32

(2) INFORMATION FOR SEQ ID NO: 11:

(i) SEQUENCE CHARACTERISTICS:
(A) LENGTH: 144 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: misc_feature
(B) LOCATION: 1..144
(D) OTHER INFORMATION: /note= "CORRESPONDS TO NUCLEOIDES 1413 TO 1556 OF SEQ ID NO:1"

(xi) SEQUENCE DESCRIPTION: SEQ ID NO: 11:

TCTTGAAAGG AGGGATGCCT AAAAACGAAG AACATTAAAA ACATATATTT GCACCGTCTA 60

ATGGATTTAT GAAAAATCAT TTTATCAGTT TGAAAATTAT GTATTATGAT AAGAAAGGGA 120

GGAAGAAAAA TGAATCCGAA CAAT 144

(2) INFORMATION FOR SEQ ID NO: 12:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 12:

CGTAATCTTA CGTCAGTAAC TTCCACAG 28

(2) INFORMATION FOR SEQ ID NO: 13:

(i) SEQUENCE CHARACTERISTICS:
(A) LENGTH: 39 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 13:

CTTAGGCTTG TTAGCTTCAC TTGTACTATG TTATTTTTG 39

(2) INFORMATION FOR SEQ ID NO: 14:

(i) SEQUENCE CHARACTERISTICS:
(A) LENGTH: 32 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 14:

GTTAGATAAG CATTTGAGGT AGAGTCCGTC CG 32

-continued (2) INFORMATION FOR SEQ ID NO: 15:

(i) SEQUENCE CHARACTERISTICS:
(A) LENGTH: 88 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO: 15:

```
TAAAGATATC TTTGAAGCTT CACGTGTTTA AACAGGCCTG CAGTAATTTC TATAGAAACT     60

TCGAAGTGCA CAAATTTGTC CGGACGTC                                        88
```

(2) INFORMATION FOR SEQ ID NO: 16:

(i) SEQUENCE CHARACTERISTICS:
(A) LENGTH: 804 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 16:

```
GGAGGAAAAG CTGTGGAGAA AATTAAAGTA TGTCTTGTGG ATGATAATAA AGAATTAGTA     60

TCAATGTTAG AGAGCTATGT AGCCGCCCAA GATGATATGG AAGTAATCGG TACTGCTTAT    120

AATGGTCAAG AGTGTTTAAA CTTATTAACA GATAAGCAAC CTGATGTACT CGTTTTAGAC    180

ATTATTATGC CACACTTAGA TGGTTTAGCT GTATTGGAAA AAATGCGACA TATTGAAAGG    240

TTAAAACAGC CTAGCGTAAT TATGTTGACA GCATTCGGGC AAGAAGATGT GACGAAAAAA    300

GCAGTTGACT TAGGTGCCTC GTATTTCATA TTAAAACCAT TTGATATGGA GAATTTAACG    360

AGTCATATTC GTCAAGTGAG TGGTAAAGCA AACGCTATGA TTAAGCGTCC ACTACCATCA    420

TTCCGATCAG CAACAACAGT AGATGGAAAA CCGAAAAACT TAGATGCGAG TATTACGAGT    480

ATCATTCATG AAATTGGTGT ACCCGCTCAT ATTAAAGGAT ATATGTATTT ACGAGAAGCA    540

ATCTCCATGG TATACAATGA TATCGAATTA TTAGGATCGA TTACGAAAGT ATTGTATCCA    600

GATATCGCAA AGAAATATAA TACAACAGCC AGCCGTGTGG AGCGCGCAAT TCGTCACGCA    660

ATTGAAGTAG CTTGGAGCCG TGGGAATATT GATTCTATTT CGTCCTTATT CGGTTATACA    720

GTATCCATGT CAAAAGCAAA ACCTACGAAC TCTGAGTTTA TCGCAATGGT TGCGGATAAG    780

CTGAGACTTG AACATAAAGC TAGT                                           804
```

(2) INFORMATION FOR SEQ ID NO: 17:

(i) SEQUENCE CHARACTERISTICS:
(A) LENGTH: 10 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO: 17:

```
CAATTAATTG                                                            10
```